United States Patent
Rioux et al.

(10) Patent No.: US 11,786,297 B2
(45) Date of Patent: *Oct. 17, 2023

(54) MINIMALLY INVASIVE ARTICULATING ASSEMBLY HAVING ABLATION CAPABILITIES

(71) Applicant: INNOBLATIVE DESIGNS, INC., Chicago, IL (US)

(72) Inventors: Robert F. Rioux, Ashland, MA (US); Alyssa Bailey, Chicago, IL (US); Tyler Wanke, Chicago, IL (US); Ryan M. Bean, Westminster, MA (US)

(73) Assignee: Innoblative Designs, Inc., Chicago, IL (US)

(*) Notice: Subject to any disclaimer, the term of this patent is extended or adjusted under 35 U.S.C. 154(b) by 688 days.

This patent is subject to a terminal disclaimer.

(21) Appl. No.: 16/633,934

(22) PCT Filed: Jul. 25, 2018

(86) PCT No.: PCT/US2018/043658
§ 371 (c)(1),
(2) Date: Jan. 24, 2020

(87) PCT Pub. No.: WO2019/023328
PCT Pub. Date: Jan. 31, 2019

(65) Prior Publication Data
US 2020/0246069 A1    Aug. 6, 2020

Related U.S. Application Data

(60) Provisional application No. 62/537,418, filed on Jul. 26, 2017.

(51) Int. Cl.
*A61B 18/14* (2006.01)
*A61B 90/00* (2016.01)
(Continued)

(52) U.S. Cl.
CPC ...... *A61B 18/1492* (2013.01); *A61B 18/1206* (2013.01); *A61B 90/37* (2016.02);
(Continued)

(58) Field of Classification Search
CPC ............ A61B 18/1492; A61B 18/1206; A61B 18/00577; A61B 2018/00577;
(Continued)

(56) References Cited

U.S. PATENT DOCUMENTS 4,205,668 A    6/1980  Criddle
4,699,147 A   10/1987  Chilson et al.
(Continued)

FOREIGN PATENT DOCUMENTS

CN    2610858 Y    4/2004
CN   104546124 A   4/2015
(Continued)

OTHER PUBLICATIONS

"Aquamantys System" Product Brochure, Medtronic, 2014 (12 Pages).
(Continued)

*Primary Examiner* — Joseph A Stoklosa
*Assistant Examiner* — Marina Delaney Templeton
(74) *Attorney, Agent, or Firm* — Brown Rudnick LLP; Matthew P. York

(57) ABSTRACT

The present invention is a minimally invasive articulating configured to be advanced through tortuous anatomy, particularly within a lung, and subsequently deliver at least two separately deployable ablation devices to a target site located at a bifurcated section of the lung (i.e., at a bronchial airway bifurcation). The pair of ablation devices are separately steerable towards respective first and second pathways extending from the bifurcation, such that each of the ablation devices can be positioned on either side of a target tissue
(Continued)

proximate the bifurcation. The first and second ablation devices include expandable distal tips configured to transition to a deployed configuration, in which each expands in diameter and is configured to apply a degree of compression and/or RF energy emission to target lung tissue (i.e., diseased tissue, such as cancer or emphysema-related damaged tissue) for subsequent ablation thereof.

18 Claims, 15 Drawing Sheets

(51) Int. Cl.
  *A61B 18/12* (2006.01)
  *A61B 18/00* (2006.01)
(52) U.S. Cl.
  CPC .............. *A61B 2018/00255* (2013.01); *A61B 2018/00541* (2013.01); *A61B 2018/00577* (2013.01); *A61B 2018/00791* (2013.01); *A61B 2018/00875* (2013.01); *A61B 2018/126* (2013.01); *A61B 2090/378* (2016.02); *A61B 2090/3762* (2016.02); *A61B 2218/002* (2013.01)
(58) Field of Classification Search
  CPC .... A61B 2018/0025; A61B 2018/1472; A61B 2018/00255; A61B 2018/00214; A61B 2018/00267; A61B 2018/00285
  See application file for complete search history.

(56) References Cited

U.S. PATENT DOCUMENTS

| | | |
|---|---|---|
| 4,976,711 A | 12/1990 | Parins et al. |
| 4,979,948 A | 12/1990 | Geddes et al. |
| 5,015,243 A | 5/1991 | Schifano |
| 5,045,056 A | 9/1991 | Behl |
| 5,052,411 A | 10/1991 | Schoolman |
| 5,100,423 A | 3/1992 | Fearnot |
| 5,117,828 A | 6/1992 | Metzger et al. |
| 5,127,411 A | 7/1992 | Schoolman et al. |
| 5,159,921 A | 11/1992 | Hoover |
| 5,163,938 A | 11/1992 | Kambara et al. |
| 5,211,639 A | 5/1993 | Wilk |
| 5,334,193 A | 8/1994 | Nardella |
| 5,429,605 A | 7/1995 | Richling: Bernd et al. |
| 5,471,982 A | 12/1995 | Edwards et al. |
| 5,472,441 A | 12/1995 | Edwards et al. |
| 5,486,161 A | 1/1996 | Lax et al. |
| 5,536,267 A | 7/1996 | Edwards et al. |
| 5,562,720 A | 10/1996 | Stern et al. |
| 5,657,760 A | 8/1997 | Ying et al. |
| 5,672,153 A | 9/1997 | Lax et al. |
| 5,672,173 A | 9/1997 | Gough et al. |
| 5,672,174 A | 9/1997 | Gough et al. |
| 5,683,384 A | 11/1997 | Gough et al. |
| 5,713,942 A | 2/1998 | Stern et al. |
| 5,728,143 A | 3/1998 | Gough et al. |
| 5,772,590 A | 6/1998 | Webster, Jr. |
| 5,782,827 A | 7/1998 | Gough et al. |
| 5,827,276 A | 10/1998 | LeVeen et al. |
| 5,840,076 A | 11/1998 | Swanson et al. |
| 5,846,239 A | 12/1998 | Swanson et al. |
| 5,855,576 A | 1/1999 | LeVeen et al. |
| 5,863,290 A | 1/1999 | Gough et al. |
| 5,868,736 A | 2/1999 | Swanson et al. |
| 5,868,776 A | 2/1999 | Wright |
| 5,871,483 A | 2/1999 | Jackson et al. |
| 5,888,198 A | 3/1999 | Eggers et al. |
| 5,891,136 A | 4/1999 | McGee et al. |
| 5,893,647 A | 4/1999 | Mochizuki |
| 5,893,847 A | 4/1999 | Kordis |
| 5,913,855 A | 6/1999 | Gough et al. |
| 5,928,229 A | 7/1999 | Gough et al. |
| 5,935,123 A | 8/1999 | Edwards et al. |
| 5,941,873 A | 8/1999 | Korenfeld |
| 5,961,513 A | 10/1999 | Swanson et al. |
| 5,980,517 A | 11/1999 | Gough |
| 6,009,877 A | 1/2000 | Edwards |
| 6,032,077 A | 2/2000 | Pomeranz |
| 6,036,689 A | 3/2000 | Tu et al. |
| 6,053,913 A | 4/2000 | Tu et al. |
| 6,053,937 A | 4/2000 | Edwards et al. |
| 6,063,081 A | 5/2000 | Mulier et al. |
| 6,071,278 A | 6/2000 | Panescu et al. |
| 6,071,280 A | 6/2000 | Edwards et al. |
| 6,099,526 A | 8/2000 | Whayne et al. |
| 6,112,123 A | 8/2000 | Kelleher et al. |
| 6,123,718 A | 9/2000 | Tu et al. |
| 6,142,993 A | 11/2000 | Whayne et al. |
| 6,221,071 B1 | 4/2001 | Sherry et al. |
| 6,241,666 B1 | 6/2001 | Pomeranz et al. |
| 6,251,109 B1 | 6/2001 | Hassett et al. |
| 6,258,087 B1 | 7/2001 | Edwards et al. |
| 6,309,352 B1 | 10/2001 | Oraevsky et al. |
| 6,312,408 B1 | 11/2001 | Eggers et al. |
| 6,312,429 B1 | 11/2001 | Burbank et al. |
| 6,315,776 B1* | 11/2001 | Edwards .............. A61B 18/148 606/41 |
| 6,358,248 B1 | 3/2002 | Mulier et al. |
| 6,379,353 B1 | 4/2002 | Nichols |
| 6,409,722 B1 | 6/2002 | Hoey et al. |
| 6,425,877 B1 | 7/2002 | Edwards |
| 6,454,766 B1 | 9/2002 | Swanson et al. |
| 6,475,213 B1 | 11/2002 | Whayne et al. |
| 6,491,710 B2 | 12/2002 | Satake |
| 6,494,902 B2 | 12/2002 | Hoey et al. |
| 6,503,247 B2 | 1/2003 | Swartz et al. |
| 6,522,930 B1 | 2/2003 | Schaer et al. |
| 6,537,248 B2 | 3/2003 | Mulier et al. |
| 6,537,272 B2 | 3/2003 | Christopherson et al. |
| 6,544,262 B2 | 4/2003 | Fleischman |
| 6,551,310 B1 | 4/2003 | Ganz et al. |
| 6,585,732 B2 | 7/2003 | Mulier et al. |
| 6,623,481 B1 | 9/2003 | Garbagnati et al. |
| 6,638,275 B1 | 10/2003 | McGaffigan et al. |
| 6,648,883 B2 | 11/2003 | Francischelli et al. |
| 6,663,622 B1 | 12/2003 | Foley et al. |
| 6,692,466 B1 | 2/2004 | Chow et al. |
| 6,736,810 B2 | 5/2004 | Hoey et al. |
| 6,736,811 B2 | 5/2004 | Panescu et al. |
| 6,743,226 B2 | 6/2004 | Cosman et al. |
| 6,764,487 B2 | 7/2004 | Mulier et al. |
| 6,770,072 B1 | 8/2004 | Truckai et al. |
| 6,780,183 B2 | 8/2004 | Jimenez, Jr. et al. |
| 6,805,131 B2 | 10/2004 | Kordis |
| 6,826,421 B1 | 11/2004 | Beally et al. |
| 6,849,073 B2 | 2/2005 | Hoey et al. |
| 6,872,206 B2 | 3/2005 | Edwards et al. |
| 6,878,149 B2 | 4/2005 | Gatto |
| 6,942,650 B1 | 9/2005 | Schultz et al. |
| 6,955,641 B2 | 10/2005 | Lubock |
| 6,978,788 B2 | 12/2005 | Klimberg et al. |
| 6,984,232 B2 | 1/2006 | Vanney et al. |
| 7,104,989 B2 | 9/2006 | Skarda |
| 7,150,745 B2 | 12/2006 | Stern et al. |
| 7,156,845 B2 | 1/2007 | Mulier et al. |
| 7,169,144 B2 | 1/2007 | Hoey et al. |
| 7,247,155 B2 | 7/2007 | Hoey et al. |
| 7,276,061 B2 | 10/2007 | Schaer et al. |
| 7,306,593 B2 | 12/2007 | Keidar et al. |
| 7,311,708 B2 | 12/2007 | McClurken |
| 7,326,208 B2 | 2/2008 | Vanney et al. |
| 7,344,535 B2 | 3/2008 | Stern et al. |
| 7,364,579 B2 | 4/2008 | Mulier et al. |
| 7,367,972 B2 | 5/2008 | Francischelli et al. |
| 7,371,231 B2 | 5/2008 | Rioux et al. |
| 7,399,299 B2 | 7/2008 | Daniel et al. |
| 7,416,552 B2 | 8/2008 | Paul et al. |
| 7,419,489 B2 | 9/2008 | Vanney et al. |
| 7,507,234 B2 | 3/2009 | Utley et al. |
| 7,507,238 B2 | 3/2009 | Edwards et al. |

(56) References Cited

U.S. PATENT DOCUMENTS

| | | |
|---|---|---|
| 7,530,979 B2 | 5/2009 | Ganz et al. |
| 7,556,628 B2 | 7/2009 | Utley et al. |
| 7,632,268 B2 | 12/2009 | Edwards et al. |
| 7,717,909 B2 | 5/2010 | Strul et al. |
| 7,769,432 B2 | 8/2010 | Klimberg et al. |
| 7,776,034 B2 | 8/2010 | Kampa |
| 7,828,793 B2 | 11/2010 | Thompson et al. |
| 7,862,498 B2 | 1/2011 | Nguyen et al. |
| 7,879,030 B2 | 2/2011 | Paul et al. |
| 7,942,873 B2 | 5/2011 | Kwan et al. |
| 7,959,627 B2 | 6/2011 | Utley et al. |
| 7,959,628 B2 | 6/2011 | Schaer et al. |
| 7,959,631 B2 | 6/2011 | DiCarlo |
| 7,993,336 B2 | 8/2011 | Jackson et al. |
| 7,997,278 B2 | 8/2011 | Utley et al. |
| 8,012,149 B2 | 9/2011 | Jackson et al. |
| 8,034,022 B2 | 10/2011 | Boatman |
| 8,043,289 B2 | 10/2011 | Behl et al. |
| 8,048,069 B2 | 11/2011 | Skwarek et al. |
| 8,114,071 B2 | 2/2012 | Woloszko et al. |
| 8,224,416 B2 | 7/2012 | de la Rama et al. |
| 8,303,584 B2 | 11/2012 | Burdio Pinilla et al. |
| 8,388,573 B1 | 3/2013 | Cox |
| 8,398,624 B2 | 3/2013 | Rioux et al. |
| 8,409,193 B2 | 4/2013 | Young et al. |
| 8,444,638 B2 | 5/2013 | Woloszko et al. |
| 8,465,484 B2 | 6/2013 | Davalos et al. |
| 8,465,486 B2 | 6/2013 | Danek et al. |
| 8,518,018 B2 | 8/2013 | Minskoff et al. |
| 8,588,886 B2 | 11/2013 | de la Rama et al. |
| 8,591,461 B2 | 11/2013 | Boatman |
| 8,617,158 B2 | 12/2013 | Garabedian et al. |
| 8,647,339 B2 | 2/2014 | Satake |
| 8,657,814 B2 | 2/2014 | Werneth et al. |
| 8,734,439 B2 | 5/2014 | Gough et al. |
| 8,814,855 B2 | 8/2014 | DiCarlo et al. |
| 8,834,461 B2 | 9/2014 | Werneth et al. |
| 8,979,838 B2 | 3/2015 | Woloszko et al. |
| 8,979,841 B2 | 3/2015 | Kunis et al. |
| 9,078,665 B2 | 7/2015 | Moss et al. |
| 9,131,980 B2 | 9/2015 | Bloom |
| 9,839,472 B2 | 12/2017 | Rioux et al. |
| 9,848,936 B2 | 12/2017 | Rioux et al. |
| 9,855,098 B2 | 1/2018 | Rioux |
| 10,070,921 B2 | 9/2018 | Rioux et al. |
| 10,342,611 B2* | 7/2019 | Rioux ................ A61B 18/1492 |
| 10,470,818 B2 | 11/2019 | Rioux et al. |
| 10,786,305 B2 | 9/2020 | Mahvi et al. |
| 11,083,519 B2 | 8/2021 | Rioux et al. |
| 2001/0031941 A1 | 10/2001 | Edwards et al. |
| 2002/0026186 A1 | 2/2002 | Woloszko et al. |
| 2002/0062123 A1 | 5/2002 | McClurken et al. |
| 2002/0087208 A1 | 7/2002 | Koblish et al. |
| 2002/0095152 A1 | 7/2002 | Ciarrocca et al. |
| 2002/0115992 A1 | 8/2002 | Utley et al. |
| 2002/0120259 A1 | 8/2002 | Lettice et al. |
| 2002/0120267 A1 | 8/2002 | Phan |
| 2002/0128641 A1 | 9/2002 | Underwood et al. |
| 2003/0009166 A1 | 1/2003 | Moutafis et al. |
| 2003/0036680 A1 | 2/2003 | Black |
| 2003/0079309 A1 | 5/2003 | Vandenbelt et al. |
| 2003/0130711 A1 | 7/2003 | Pearson et al. |
| 2003/0163128 A1 | 8/2003 | Patil et al. |
| 2003/0216725 A1 | 11/2003 | Woloszko et al. |
| 2003/0225403 A1 | 12/2003 | Woloszko et al. |
| 2003/0233099 A1* | 12/2003 | Danaek ............... A61B 18/1477 606/113 |
| 2004/0049165 A1 | 3/2004 | Thompson et al. |
| 2004/0087936 A1 | 5/2004 | Stern et al. |
| 2004/0092960 A1 | 5/2004 | Abrams et al. |
| 2004/0122352 A1 | 6/2004 | John |
| 2005/0004535 A1 | 1/2005 | Schklair |
| 2005/0049454 A1 | 3/2005 | Ouchi |
| 2005/0054993 A1 | 3/2005 | Falahee |
| 2005/0059965 A1 | 3/2005 | Eberl et al. |
| 2005/0070894 A1 | 3/2005 | McClurken |
| 2005/0154386 A1 | 7/2005 | West et al. |
| 2005/0187491 A1 | 8/2005 | Burbank et al. |
| 2006/0069385 A1 | 3/2006 | Lafontaine et al. |
| 2006/0212032 A1 | 9/2006 | Daniel et al. |
| 2006/0259027 A1 | 11/2006 | Kwan et al. |
| 2007/0083195 A1 | 4/2007 | Werneth et al. |
| 2007/0100201 A1 | 5/2007 | Komiya et al. |
| 2008/0004534 A1 | 1/2008 | Gelbart et al. |
| 2008/0015565 A1 | 1/2008 | Davison |
| 2008/0103494 A1 | 5/2008 | Rioux et al. |
| 2008/0140001 A1 | 6/2008 | Globerman et al. |
| 2008/0234673 A1 | 9/2008 | Marion et al. |
| 2009/0171340 A1 | 7/2009 | Young |
| 2009/0177193 A1 | 7/2009 | Wang et al. |
| 2009/0248021 A1 | 10/2009 | McKenna |
| 2009/0292177 A1 | 11/2009 | Eggers et al. |
| 2009/0299355 A1* | 12/2009 | Bencini ............... A61B 18/02 606/21 |
| 2010/0114087 A1 | 5/2010 | Edwards et al. |
| 2010/0256629 A1 | 10/2010 | Wylie et al. |
| 2010/0292689 A1 | 11/2010 | Davison et al. |
| 2010/0330893 A1 | 12/2010 | Turner et al. |
| 2011/0172485 A1* | 7/2011 | Lubock ............... A61N 5/1015 600/3 |
| 2011/0257646 A1 | 10/2011 | Utley et al. |
| 2012/0029510 A1 | 2/2012 | Haverkost |
| 2012/0029511 A1 | 2/2012 | Smith et al. |
| 2012/0059437 A1 | 3/2012 | Shalev |
| 2012/0109250 A1 | 5/2012 | Cates et al. |
| 2012/0172680 A1 | 7/2012 | Gelfand et al. |
| 2012/0271253 A1 | 10/2012 | Schultz |
| 2012/0289776 A1 | 11/2012 | Keast et al. |
| 2013/0030425 A1 | 1/2013 | Stewart et al. |
| 2013/0085493 A1* | 4/2013 | Bloom ............... A61B 18/1492 606/41 |
| 2013/0109924 A1 | 5/2013 | Gan |
| 2013/0131649 A1 | 5/2013 | Hughett, Sr. et al. |
| 2013/0158536 A1 | 6/2013 | Bloom |
| 2013/0172870 A1 | 7/2013 | Germain et al. |
| 2013/0184702 A1 | 7/2013 | Neal, II et al. |
| 2013/0184706 A1 | 7/2013 | Gelbart et al. |
| 2013/0253506 A1 | 9/2013 | Rioux et al. |
| 2013/0274728 A1 | 10/2013 | Kapur et al. |
| 2013/0310833 A1 | 11/2013 | Brown et al. |
| 2013/0338662 A1 | 12/2013 | Weber |
| 2014/0018788 A1* | 1/2014 | Engelman .......... A61B 18/1492 606/33 |
| 2014/0018794 A1* | 1/2014 | Anderson ........... A61B 18/1492 606/41 |
| 2014/0031810 A1 | 1/2014 | Mahvi et al. |
| 2014/0039491 A1 | 2/2014 | Bakos et al. |
| 2014/0058343 A1 | 2/2014 | Schultz |
| 2014/0058376 A1 | 2/2014 | Horn et al. |
| 2014/0180273 A1 | 6/2014 | Nair |
| 2014/0221998 A1 | 8/2014 | Latterell |
| 2014/0228801 A1 | 8/2014 | Keeling |
| 2014/0276731 A1 | 9/2014 | Voegele et al. |
| 2014/0276748 A1 | 9/2014 | Ku et al. |
| 2014/0296842 A1 | 10/2014 | Mansi et al. |
| 2014/0378960 A1 | 12/2014 | Fischer et al. |
| 2015/0018817 A1 | 1/2015 | Willard |
| 2015/0141982 A1* | 5/2015 | Lee ...................... A61B 5/6853 606/41 |
| 2015/0306361 A1 | 10/2015 | Feig et al. |
| 2016/0015444 A1 | 1/2016 | Wittenberger |
| 2016/0045197 A1 | 2/2016 | Mitelberg et al. |
| 2016/0113707 A1 | 4/2016 | Sahakian et al. |
| 2016/0113708 A1 | 4/2016 | Moss et al. |
| 2016/0117221 A1 | 4/2016 | Nair et al. |
| 2016/0184008 A1 | 6/2016 | Papaioannou et al. |
| 2016/0317221 A1 | 11/2016 | Rioux |
| 2017/0000559 A1 | 1/2017 | Rioux et al. |
| 2017/0027633 A1 | 2/2017 | Wham et al. |
| 2017/0119454 A1* | 5/2017 | Rioux ................ A61B 18/1482 |
| 2017/0172646 A1 | 6/2017 | Patel et al. |
| 2017/0215947 A1 | 8/2017 | Rioux et al. |
| 2017/0215951 A1 | 8/2017 | Wang et al. |
| 2017/0252092 A1 | 9/2017 | Rioux et al. |

(56) References Cited

U.S. PATENT DOCUMENTS

| | | |
|---|---|---|
| 2017/0281255 A1 | 10/2017 | Babini et al. |
| 2017/0281267 A1 | 10/2017 | Rioux et al. |
| 2017/0281271 A1 | 10/2017 | Rioux |
| 2018/0014880 A1 | 1/2018 | Rioux et al. |
| 2018/0076336 A1 | 3/2018 | De Graff et al. |
| 2018/0078305 A1 | 3/2018 | Rioux et al. |
| 2018/0104004 A1 | 4/2018 | Rioux et al. |
| 2018/0132833 A1 | 5/2018 | Gotlib |
| 2018/0153637 A1 | 6/2018 | Al-Shawi et al. |
| 2019/0314084 A1 | 10/2019 | Rioux |
| 2021/0275244 A1 | 9/2021 | Rioux et al. |

FOREIGN PATENT DOCUMENTS

| | | |
|---|---|---|
| DE | 102010032932 A1 | 2/2012 |
| EP | 0777445 B1 | 6/1999 |
| EP | 2942023 A3 | 2/2016 |
| EP | 3040043 B1 | 1/2018 |
| JP | 3009735 B2 | 2/2000 |
| JP | 2010-505596 A | 2/2010 |
| JP | 2010-155083 A | 7/2010 |
| JP | 2013-532552 A | 8/2013 |
| JP | 2015-100706 A | 6/2015 |
| JP | 2016-127919 A | 7/2016 |
| WO | 9510326 A1 | 4/1995 |
| WO | 9942047 A1 | 8/1999 |
| WO | 0051683 A1 | 9/2000 |
| WO | 01/74252 A2 | 10/2001 |
| WO | 2007103986 A2 | 9/2007 |
| WO | 2011143468 A2 | 11/2011 |
| WO | 2012015722 A1 | 2/2012 |
| WO | 2012050637 A1 | 4/2012 |
| WO | 2013134733 A3 | 11/2013 |
| WO | 2014022379 A1 | 2/2014 |
| WO | 2014189887 A2 | 11/2014 |
| WO | 2015/142674 A1 | 9/2015 |
| WO | 2015163846 A1 | 10/2015 |
| WO | 2015200518 A1 | 12/2015 |
| WO | 2016/176567 A1 | 11/2016 |
| WO | 2016/181316 A1 | 11/2016 |
| WO | 2016181318 A1 | 11/2016 |
| WO | 2019023328 A1 | 1/2019 |

OTHER PUBLICATIONS

"Starburst Talon" Specifications Brochure, Angiodynamics, 2013 (2 Pages).

Extended European Search Report issued in European Application No. 13825361.2, dated Jun. 10, 2016, 13 pages.

Extended European Search Report issued in European Application No. 16787228.2, dated Nov. 27, 2018, 6 pages.

Extended European Search Report issued in European Application No. 16860886.7, dated Jun. 12, 2019, 8 pages.

Extended European Search Report issued in European Application No. 17747970.6, dated Jul. 16, 2019, 6 pages.

Extended European Search Report issued in European Application No. 17828289.3, dated Feb. 6, 2020, 5 pages.

Extended European Search Report issued in European Application No. 17895158.8, dated Feb. 28, 2020, 8 pages.

Extended European Search Report issued in European Application No. 19219030.4, dated Jun. 26, 2020, 6 pages.

International Search Report and Written Opinion of the Interational Searching Authority dated Feb. 27, 2018 for International Application No. PCT/US2017/056754 (11 Pages).

International Search Report and Written Opinion of the International Searching Authority dated Aug. 22, 2016 for International Application No. PCT/US2016/030081 (11 Pages).

International Search Report and Written Opinion of the International Searching Authority dated Aug. 26, 2018 for International Application No. PCT/US2017/059850 (10 Pages).

International Search Report and Written Opinion of the International Searching Authority dated Aug. 5, 2015 for International Application No. PCT/US2015/020596 (13 Pages).

International Search Report and Written Opinion of the International Searching Authority dated Feb. 2, 2017 for International Application No. PCT/US2016/059345 (10 Pages).

International Search Report and Written Opinion of the International Searching Authority dated Jun. 11, 2017 for International Application No. PCT/US2017/019398 (27 Pages).

International Search Report and Written Opinion of the International Searching Authority dated May 16, 2017 for International Application No. PCT/US2017/015582 (11 pages).

International Search Report and Written Opinion of the International Searching Authority dated May 16, 2017 for International Application No. PCT/US2017/015584 (11 pages).

International Search Report and Written Opinion of the International Searching Authority dated Nov. 1, 2018 for International Application No. PCT/US2018/043654 (10 Pages).

International Search Report and Written Opinion of the International Searching Authority dated Nov. 29, 2013 for International Application No. PCT/US2013/052703 (11 Pages).

International Search Report and Written Opinion of the International Searching Authority dated Oct. 19, 2017 for International Application No. PCT/US2017/041501 (63 Pages).

International Search Report and Written Opinion of the International Searching Authority dated Sep. 16, 2018 for International Application No. PCT/US2018/036268 (11 Pages).

International Search Report and Written Opinion of the International Searchng Authority dated Jun. 6, 2018 for International Application No. PCT/US2018/019151 (17 Pages).

Medtronic, "Aquamantys Bipolar Sealers." Electrosurgical Products, Jun. 2017. Retrieved Jul. 21, 2017. <http://www.medtronic.com/us-en/healthcare-professionals/products/general-surgery/electrosurgical/aquamantys-bipolar-sealers.html> (11 Pages).

Non-Final Office Action dated Aug. 11, 2017 for U.S. Appl. No. 15/337,334 (11 Pages).

Non-Final Office Action dated Aug. 11, 2017 for U.S. Appl. No. 15/624,327 (11 Pages).

Non-Final Office Action dated Aug. 4, 2017 for U.S. Appl. No. 15/624,230 (18 Pages).

Non-Final Office Action dated May 7, 2018 for U.S. Appl. No. 15/142,616 (13 Pages).

Notice of Allowance dated Jul. 24, 2018 for U.S. Appl. No. 15/784,778 (12 Pages).

Official Action issued in Japanese Patent Application No. 2018-540040, dated Jun. 19, 2019, 11 pages.

Response to Non-Final Office Action Filed Sep. 19, 2017 for U.S. Appl. No. 15/624,327 (8 Pages).

Response to Non-Final Office Action Filed Sep. 20, 2017 for U.S. Appl. No. 15/337,334 (6 Pages).

Response to Non-Final Office Action Filed Sep. 20, 2017 for U.S. Appl. No. 15/624,230 (10 Pages).

International Search Report and Written Opinion issued in International Application No. PCT/US2018/043658, dated Nov. 15, 2018 (13 pages).

International Search Report and Written Opinion issued in International Application No. PCT/US2020/033357, dated Aug. 27, 2020 (5 pages).

ISA—Search Strategy—Issued by the Israel Patent Office for International Application No. PCT/US2018/043658, dated Nov. 14, 2018 (1 page).

Office Action issued in U.S. Appl. No. 16/633,765, dated Nov. 5, 2021, 9 pages.

International Search Report and Written Opinion of the International Searching Authority dated Aug. 27, 2020 for International Application No. PCT/US2020/033355 (4 pages).

Non-Final Office Action issued in U.S. Appl. No. 16/001,494, dated Nov. 26, 2021, 18 pages.

Chinese Office Action and English summary issued in Chinese Application No. 201680062908.2, dated Jun. 30, 2020, 12 pages.

Extended European Search Report issued in European Application No. 18757994.1, dated Nov. 24, 2020, 8 pages.

Extended European Search Report issued in European Patent Application No. 18812643.7, dated Feb. 9, 2021, 7 pages.

Japanese Office Action and English translation issued in Japanese Application No. 2018-521973, dated Nov. 4, 2020, 8 pages.

(56) References Cited

OTHER PUBLICATIONS

Non-Final Office Action issued in U.S. Appl. No. 16/876,284, dated Apr. 19, 2022, 13 pages.
Extended European Search Report issued European Patent Application No. 18839274.0, dated Mar. 15, 2021, 9 pages.
Extended European Search Report issued in European Patent Application No. 18839345.8, dated Mar. 12, 2021, 9 pages.
International Search Report and Written Opinion of the International Searching Authority dated Aug. 27, 2020 for International Application No. PCT/US2020/033355 (5 pages).
ISA—Search Strategy for PCT International Application No. PCT/US2018/043658.
International Search Report dated Nov. 15, 2018 in connection with PCT International Application No. PCT/US2018/043658.
Written Opinion of the International Searching Authority dated Nov. 15, 2018 in connection with PCT International Application No. PCT/US2018/043658.
International Search Report and Written Opinion issued in International Application No. PCT/US2022/011296, dated Mar. 25, 2022, 9 pages.
International Search Report and Written Opinion issued in International Application No. PCT/US2022/041881, dated Dec. 13, 2022, 26 pages.
Final Rejection issued in U.S. Appl. No. 16/876,284, dated Aug. 12, 2022, 14 pages.
European Office Action issued in European Application No. 18839345.8, dated May 23, 2022, 4 pages.

\* cited by examiner

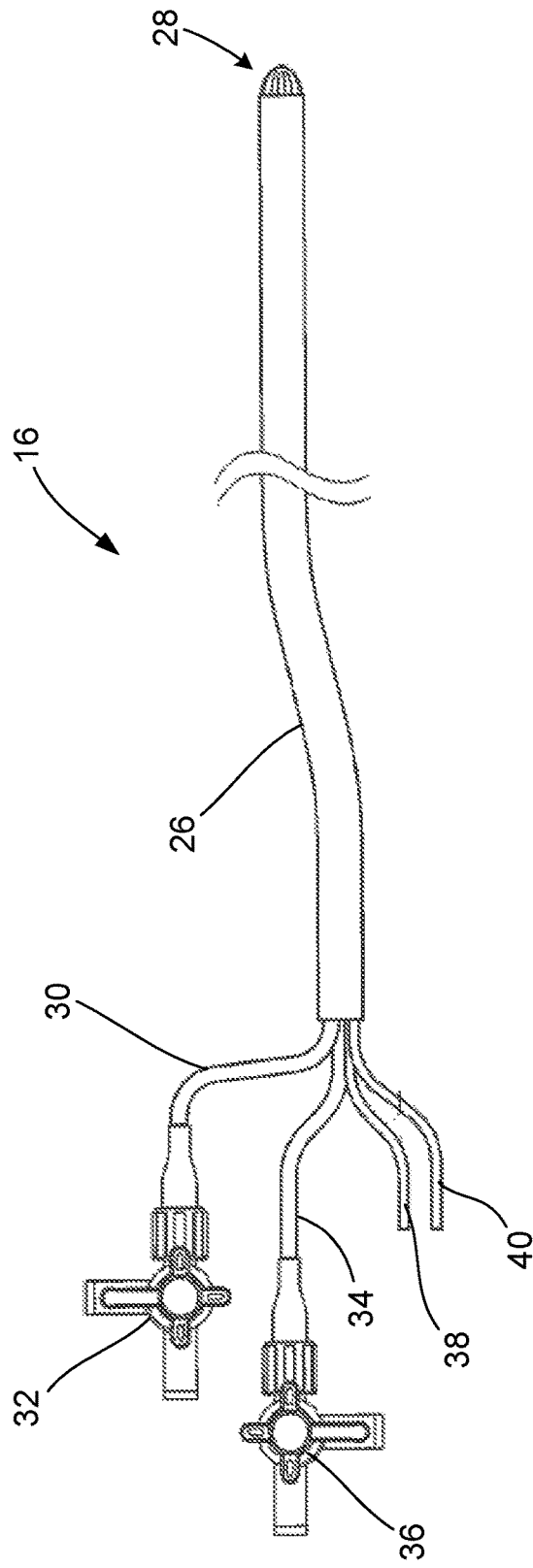
FIG. 2
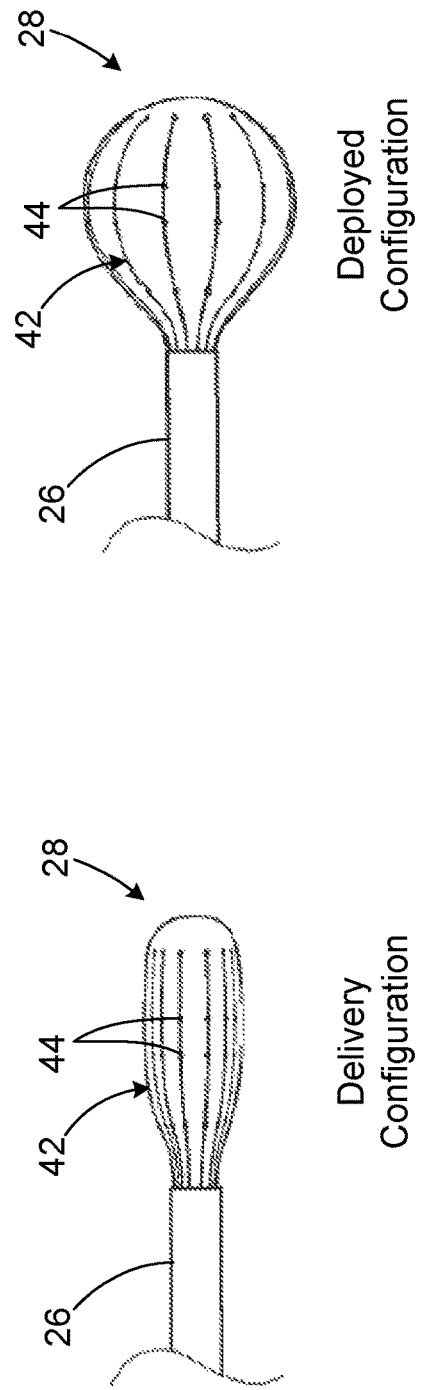
FIG. 3A
Delivery Configuration
FIG. 3B
Deployed Configuration Positioning of distal tips of first and second ablation devices on either side of bifurcation Expansion of distal tips of
first and second ablation
devices Deployment of distal tips of
first and second ablation
devices Completion of ablation procedure Ablation of tumor/diseased tissue Emission of RF energy from distal tip(s)

Advancement of guide sheath towards distal tips to draw distal tips toward one another Deployment of distal tips of first and second ablation devices Ablation of tumor/diseased tissue

MINIMALLY INVASIVE ARTICULATING ASSEMBLY HAVING ABLATION CAPABILITIES

CROSS-REFERENCE TO RELATED APPLICATIONS

This application is a national stage of International Application Number PCT/US2018/043658, filed Jul. 25, 2018, which was published as International Publication No. WO 2019/023328 on Jan. 31, 2019, and which claims the benefit of, and priority to, U.S. Provisional Application No. 62/537,418, filed Jul. 26, 2017, the contents of each of which is hereby incorporated by reference herein in its entirety.

FIELD

The present disclosure relates generally to medical devices for ablating tissue, and, more particularly, to a minimally invasive articulating assembly including a delivery device in the form of a guide sheath configured to be advanced through tortuous anatomy, particularly within a lung, and deliver at least two separate steerable and expandable ablation devices to a target site located at a bifurcated section within the lung (e.g., bronchial airway bifurcation), wherein the expandable ablation devices are configured to be deployed and cooperatively controlled so as to apply compression and/or energy emission to the target tissue for subsequent ablation thereof.

BACKGROUND

Ablation therapy is a type of minimally invasive procedure medical professionals (i.e., surgeons) use to destroy abnormal tissue that occurs with many conditions. For example, a doctor might use an ablation procedure to treat a cancerous tumor (i.e., completely destroy cancerous tissue) or to destroy (ablate) a small amount of tissue, such as in the heart so as to prevent and/or treat abnormal heart rhythms. In some instances, ablation therapy may be particularly difficult due to the location of the abnormal tissue to be treated and the degree of preciseness required to avoid ablating adjacent healthy tissue, such as diseases of the lung.

For example, emphysema is a lung condition that causes shortness of breath. In people with emphysema, the air sacs in the lungs (alveoli) are damaged. Over time, the inner walls of the air sacs weaken and rupture, thereby creating larger air spaces instead of many small ones, which reduces the surface area of the lungs and, in turn, the amount of oxygen that reaches the bloodstream. A currently available solution for patients suffering from emphysema is a surgical procedure called Lung Volume Reduction (LVR) surgery whereby diseased lung is resected and the volume of the lung is reduced. Such a procedure allows healthier lung tissue to expand into the volume previously occupied by the diseased tissue and allows the diaphragm to recover. However, high mortality and morbidity may be associated with this invasive procedure.

Several minimally invasive investigational therapies exist that aim at improving the quality of life and restoring lung function for patients suffering from emphysema, such as mechanical implants in the form of one-way valve devices, which achieve absorptive atelectasis of a lung (i.e., the collapse of part of the lung) by preventing air from entering diseased portion of the lung, while allowing air and mucous to pass through the device out of the diseased regions. However, such devices may lack effectiveness. In particular, studies have shown that a phenomenon known as collateral ventilation, which is the ventilation of alveolar structure through passages or channels that bypass normal airway and thus prevent complete occlusion, prevents atelectasis. The lack of atelectasis or lung volume reduction drastically reduces the effectiveness of currently known mechanical implants. Other mechanical devices include means of deploying anchors into airways and physically deforming airways by drawing the anchors together via cables. Biological treatments may utilize tissue engineering aimed at causing scarring at specific locations. Unfortunately, it can be difficult to control the scarring and to prevent uncontrolled proliferation of scarring.

SUMMARY

The present invention is directed to a minimally invasive articulating assembly including a delivery device in the form of a guide sheath configured to be advanced through tortuous anatomy, particularly within a lung, and subsequently deliver at least two separately deployable and expandable ablation devices to a target site located at a bifurcated section of the lung (i.e., at a bronchial airway bifurcation) for ablation of a target tissue (i.e., diseased tissue, such as a cancerous tumor or emphysema-related damaged tissue).

A first one of the ablation devices is steerable towards a first pathway extending from the bifurcation and a second one of the ablation devices is separately steerable towards a second pathway extending from the bifurcation, such that each of the ablation devices can be positioned on either side of a target tissue proximate the bifurcation. The first and second ablation devices each include a distal applicator tip configured to transition between a delivery configuration, in which the applicator tip is collapsed and is shaped and sized to fit within and pass through a pathway (i.e., bronchial airway), and a deployed configuration, in which the applicator tip is expanded and is shaped and sized in such a manner so as to become lodged or anchored within the pathway and thereby apply at least a degree of compression upon the target tissue, such that the target tissue is generally compressed between the distal applicator tips. One or both of the distal applicator tips further includes an electrode array configured to emit RF energy upon the target tissue for subsequent ablation thereof.

Accordingly, the assembly of the present invention allows for improved controlled over the ablation of tissue, particularly in normally isolated regions ((i.e., tortuous pathways in the lung), allowing for application of RF energy in a controlled manner with little or no deleterious effect on surrounding healthy tissue or organs. Furthermore, the present invention allows for debulking of diseased tissue almost immediately by way of RF ablation, such that, upon treating the diseased tissue, necrosis of such tissue is immediate and the assembly can be completely removed once the procedure is completed, and thus does not present any issues that may be present with devices requiring implantation for a given period of time.

BRIEF DESCRIPTION OF THE DRAWINGS

Features and advantages of the claimed subject matter will be apparent from the following detailed description of embodiments consistent therewith, which description should be considered with reference to the accompanying drawings, wherein:

FIG. 2 is a perspective view of one embodiment of a steerable and expandable ablation device compatible with the system of FIG. 1A;

FIGS. 3A and 3B are enlarged views of a distal applicator tip of the ablation device of FIG. 2 in greater detail, illustrating transition of the applicator tip between a delivery configuration (FIG. 3A) and a deployed configuration (FIG. 3B);

Figure 1A:
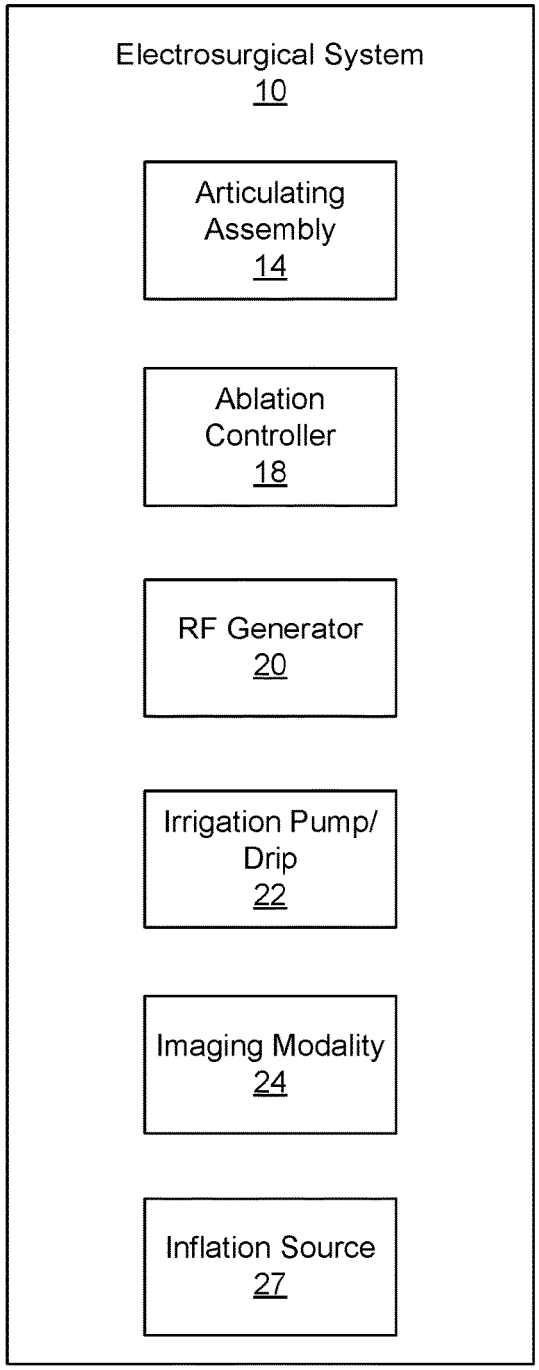
FIGS. 1A and 1B are schematic illustrations of an ablation system consistent with the present disclosure.

For a thorough understanding of the present disclosure, reference should be made to the following detailed description, including the appended claims, in connection with the above-desribed drawings. Although the present disclosure is described in connection with exemplary embodiments, the disclosure is not intended to be limited to the specific forms set forth herein. It is understood that various omissions and substitutions of equivalents are contemplated as circumstances may suggest or render expedient.

DETAILED DESCRIPTION

By way of overview, the present disclosure is generally directed to a minimally invasive articulating assembly configured to be delivered to a surgical site within a patient and further configured to be advanced through a tortuous anatomy to reach a target tissue and subsequently provide ablation treatment to the target tissue. In particular, the articulating assembly includes a delivery device in the form of a scope or other access device configured to provide access to a target site within a patient. The delivery device has an outer guide sheath configured to be advanced through the tortuous anatomy, particularly within a lung, and subsequently deliver at least two separately deployable and expandable ablation devices to the target site located at a bifurcated section of the lung (i.e., at a bronchial airway bifurcation) for ablation of the target tissue, which may include diseased lung tissue, including, but not limited to, a cancerous tumor or emphysema-related damaged tissue.

A first one of the ablation devices is steerable towards a first pathway extending from the bifurcation and a second one of the ablation devices is separately steerable towards a second pathway extending from the bifurcation, such that each of the ablation devices can be positioned on either side of a target tissue proximate the bifurcation. The first and second ablation devices each include a distal applicator tip configured to transition between a delivery configuration, in which the applicator tip is collapsed and is shaped and sized to fit within and pass through a pathway (i.e., bronchial airway), and a deployed configuration, in which the applicator tip is expanded and is shaped and sized in such a manner so as to become lodged or anchored within the pathway and thereby apply at least a degree of compression upon the target tissue, such that the target tissue is generally compressed between the distal applicator tips. One or both of the distal applicator tips further includes an electrode array configured to emit RF energy upon the target tissue for subsequent ablation thereof.

Accordingly, the assembly of the present invention allows for improved controlled over the ablation of tissue, particularly in normally isolated regions ((i.e., tortuous pathways in the lung), allowing for application of RF energy in a controlled manner with little or no deleterious effect on surrounding healthy tissue or organs. Furthermore, the present invention allows for debulking of diseased tissue almost immediately by way of RF ablation, such that, upon treating the diseased tissue, necrosis of such tissue is immediate and the assembly can be completely removed once the procedure is completed, and thus does not present any issues that may be present with devices requiring implantation for a given period of time.

For ease of description and explanation, the following description focuses on the use of the articulating assembly within the tortuous passageways of the lung of a patient. However, it should be noted that the present invention can be used in any other organs which may include tortuous pathways, such as the heart or the vascular system, and which may further include bifurcations.

Figure 1B:
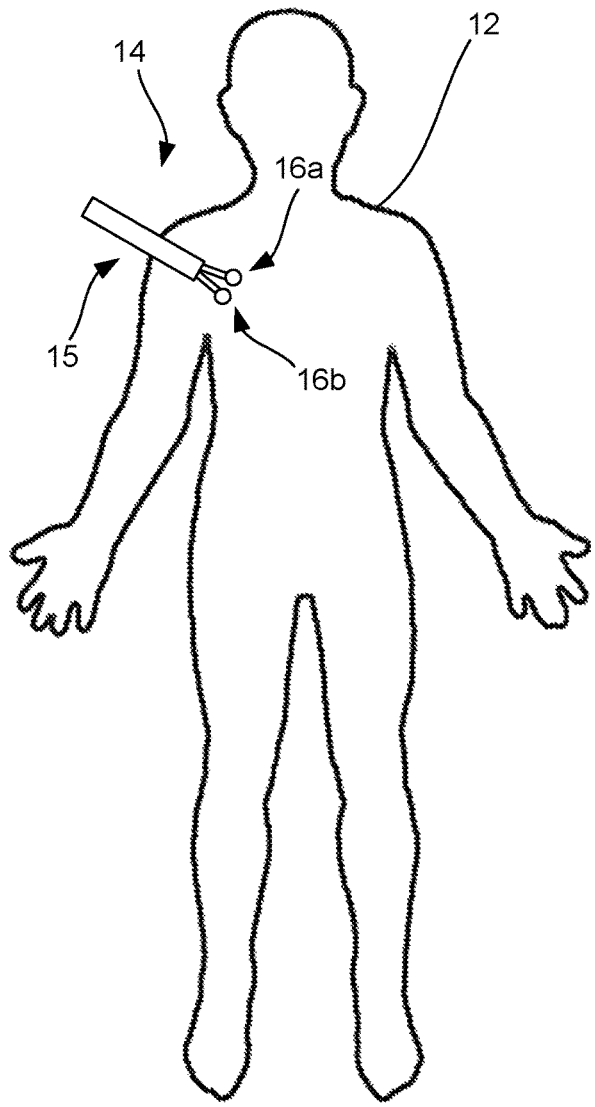

FIGS. 1A and 1B are schematic illustrations of an ablation system 10 for providing ablation of diseased tissue within a patient 12. The ablation system 10 generally includes an articulating assembly 14, including a delivery device 15, which may be in the form of a scope or other access device configured to provide access to a target site within the patient 12. The delivery device 15 is configured to be advanced through the tortuous anatomy, particularly within a lung, and subsequently deliver at least two separately deployable and expandable ablation devices 16a, 16b to the target site for ablation of a target tissue, as will be described in greater detail herein. The articulating assembly 14, specifically each of the first and second ablation devices 16a, 16b may further be coupled to a controller 18, an ablation RF generator 20, and an irrigation pump or drip 22.

As will be described in greater detail herein, each of the ablation devices 16a, 16b includes a distal applicator tip or portion configured to be advanced to the target site and transition between a delivery configuration, in which the tip is collapsed and shaped and sized to fit within and pass through a pathway (i.e., bronchial airway), and a deployed configuration, in which the applicator tip is expanded and is shaped and sized in such a manner so as to become lodged or anchored within the pathway and thereby apply at least a degree of compression upon the target tissue (e.g., an expanded spherical shape). The distal applicator tip is configured to emit non-ionizing radiation, such as radiofrequency (RF) energy, to treat the target tissue, specifically a diseased tissue, such as a cancerous tumor or emphysema-related damaged tissue within the lung. For example, the applicator tip of each ablation device generally includes an electrode array positioned along an external surface thereof, wherein the electrode array is configured to receive an electrical current from an energy source (i.e., from the RF generator 20) and conduct energy, the energy including RF energy. The ablation controller 18 may be used to control the emission of energy from the electrode array of a distal tip of an ablation device 16 to result in ablation, as well as control parameters of the ablation (i.e., elapsed time, total energy output, specific energy output pattern, etc.).

In some embodiments, each ablation device 16 may be further configured to provide RF ablation via a virtual electrode arrangement, which includes distribution of a fluid along an exterior surface of the distal tip and, upon activation of the electrode array, the fluid may carry, or otherwise promote, energy emitted from the electrode array to the surrounding tissue. In particular, the distal tip of an ablation device may include a plurality of ports or apertures configured to allow the fluid to pass therethrough, or weep, from an interior of the distal tip to an external surface of the distal tip. Accordingly, the irrigation pump or drip 22 may provide the conductive fluid (e.g., saline) to the distal tip of each ablation device.

As will be described in greater detail herein, during an ablation treatment, the RF generator 20 may generally provide RF energy (e.g., electrical energy in the radiofrequency (RF) range (e.g., 350-800 kHz)) to an electrode array of one of the ablation devices 16, as controlled by the ablation controller 18. At the same time, saline may also be released from the irrigation pump or drip 22 the distal tip of the ablation device 16.

The ablation system 10 may further include an imaging modality 24. For example, during a procedure, the imaging modality 24 may provide an operator (e.g., surgeon) with a visual depiction of distal end of the delivery device 15 during advancement towards the target site and may further provide visual depiction of the ablation devices 16a, 16b during delivery and deployment thereof when positioning for subsequent ablation of target tissue. For example, in some embodiments, the imaging modality 24 may be configured to receive sensing input from the delivery device 15, the ablation devices 16a, 16b (e.g., sensors on the scope 15 and/or ablation devices 16a, 16b, such as ultrasound, video, images, etc.) so as to provide an accurate display to the surgeon during a procedure. The imaging modality 24 may provide a medical imaging procedure, including, but not limited to, ultrasound (US), wavelength detection, X-ray-based imaging, illumination, computed tomography (CT), radiography, and fluoroscopy, or a combination thereof, such that, when viewed under such a medical imaging procedure provided by the imaging modality 24, the visibility of the target site is enhanced and a surgeon can better maneuver the scope 15 and each of the first and second ablation devices 16a, 16b during a procedure.

FIG. 2 is a perspective view of one embodiment of a steerable and expandable ablation device 16 compatible with the articulating assembly 14. As shown, the ablation device 16 generally includes a guide sheath 26 sized or shaped to fit within the delivery device 15. The ablation device 16 further includes a distal applicator tip 28 configured to extend from a distal end of the guide sheath 26. The tip 28 generally includes a flexible body configured to have a collapsed configuration and entirely fit within the lumen of the guide sheath 26, such that, upon advancing the guide sheath 26 to the target site, the tip 28 can be extended from the distal end of the guide sheath 26 and the surgeon can control transitioning of the tip 28 from a delivery configuration to a deployed configuration. When in the delivery configuration (as shown in FIG. 3A), the tip 28 is collapsed and is shaped and sized to fit within and pass through a pathway (i.e., bronchial airway). When in the deployed configuration (as shown in FIG. 3B), the tip 28 is expanded in response to inflation of the tip 28. For example, in some embodiments, the tip 28 may include an inner balloon (not shown) configured to receive a fluid or gas via a line 30 coupled to a source controllable via a controller, such as a valve 32 or the like. Upon inflation of the inner balloon, the tip 28 may correspondingly expand to assume the deployed configuration. The tip 28 is further coupled to the irrigation pump or drip 22 via a fluid line 34, in which the flow of conductive fluid from the irrigation pump or drip 22 to the tip 28 may be controlled manually via a valve 36 or the like. Accordingly, the tip 28 may include a design similar to the ablation device design described in U.S. application Ser. No. 15/142,616, filed Apr. 29, 2016 (Publication No. 2016/0317221), the content of which is incorporated by reference herein in its entirety.

As will be described in greater detail herein, the ablation device 16 is steerable by way of a pull wire or tether that is anchored to a distal end of the guide sheath 26, thereby allowing maneuverability of the tip 28 when advancing the ablation device 16 through bronchial airways. The pull wire or tether may be housed within a sheath 38 housing the pull wire or tether, for example. As generally understood, application of a pulling force upon the pull wire will generally result in a corresponding deflection of the distal end of the guide sheath 26, thereby allowing for the ablation device to be maneuvered past bifurcations or other obstructions.

As previously described herein, the ablation device 16 may further include sensors or the like to assist in providing visualization of the device to a surgeon during a procedure. Thus, in some embodiments, the ablation device may include a sensor, including, for example, an ultrasound transducer positioned along the guide sheath 26 adjacent to a distal end thereof or placed upon the tip 28 body, wherein a line providing signal from the sensor may be housed within a sheath 40. Furthermore, the electrical line (not shown) coupling the RF generator 20 to an electrode array on the tip 28 may further be housed within a separate sheath (not shown).

As shown in FIGS. 3A and 3B, the tip 28 includes an electrode array is composed of a plurality of conductive members (e.g., conductive wires) 42. In some embodiments, each of the plurality of conductive wires 42, or one or more sets of a combination of conductive wires 42, is configured to independently receive an electrical current from the RF generator 20 and independently conduct energy, the energy including RF energy. This allows energy to be selectively delivered to a designated conductive wire or combination of conductive wires. This design also enables the ablation device 16 to function in a bipolar mode because a first conductive wire (or combination of conductive wires) can deliver energy to the surrounding tissue through its electrical connection with the RF generator while a second conductive wire (or combination of conductive wiress) can function as a ground or neutral conductive member.

In some embodiments, the ablation device 16 is configurd to provide RF ablation via a virtual electrode arrangement, which includes distribution of a fluid along an exterior surface of the distal tip 28 and, upon activation of the electrode array, the fluid may carry, or otherwise promote, energy emitted from the electrode array to the surrounding tissue. For example, as previously described, the tip 28 includes an interior chamber configured to receive the conductive fluid thereoin from the fluid source. The tip 28 body includes a plurality of ports, ports, or apertures 44 configured to allow the fluid to pass therethrough, or weep, from the interior chamber to an external surface of the tip 28. Accordingly, upon positioning the tip 28 at a target site and subsequently deploying the tip 28 (i.e., transitioning the tip 28 from the delivery configuration to the deployed configuration shown in FIG. 3B) the electrode array can be activated and fluid can be delivered to the tip 28. The fluid weeping through the ports 44 to the outer surface of the tip 28 is able to carry energy from electrode array, thereby creating a virtual electrode. Accordingly, upon the fluid weeping through the ports, a pool or thin film of fluid is formed on the exterior surface of the tip 28 and is configured to ablate surrounding tissue via the RF energy carried from the electrode array.

Figure 4:
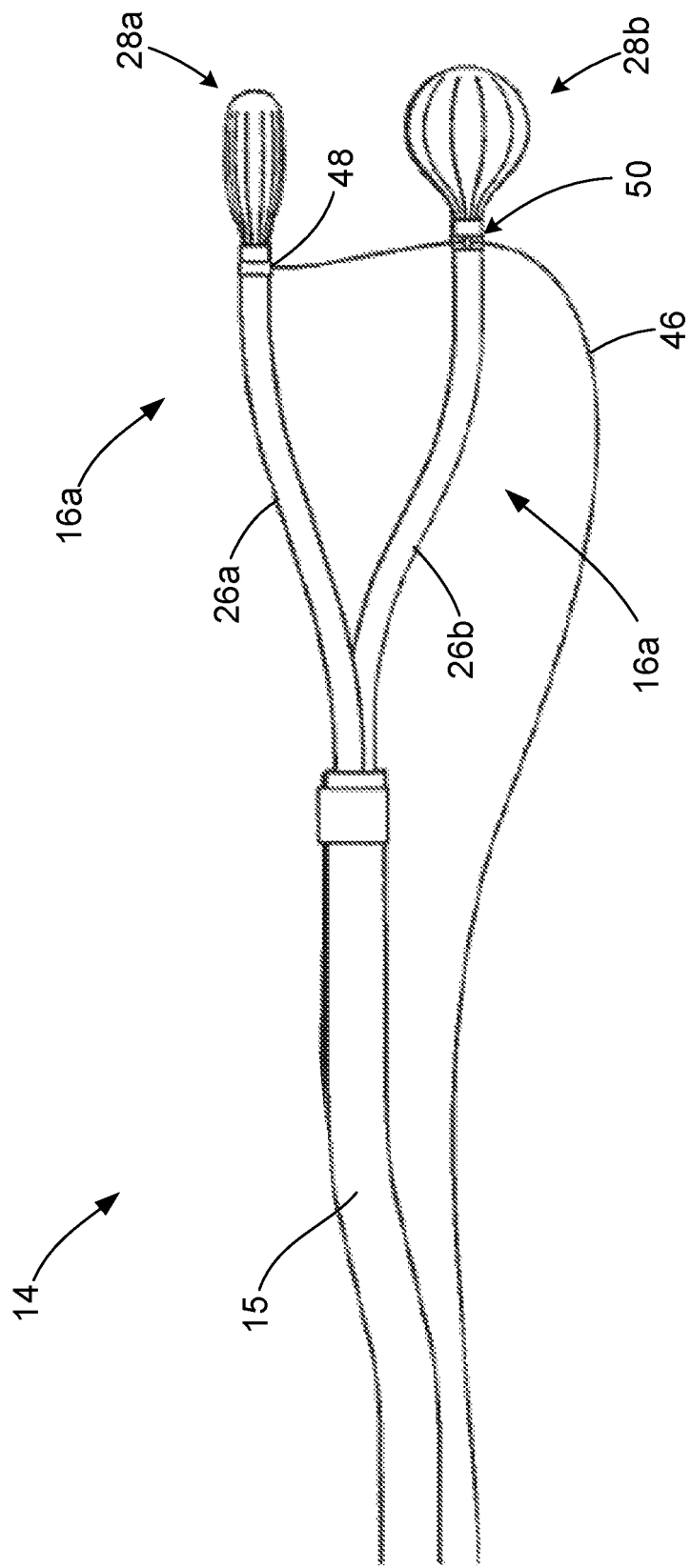
FIG. 4 is a side view of an articulating assembly consistent with the present disclosure, illustrating a pair of steerable and expandable ablation devices extended from an delivery device, wherein the distal tip of the first ablation device is in the delivery configuration and the distal tip of the second ablation device is in the deployed configuration.

FIG. 4 is a side view of an articulating assembly 14 illustrating a pair of steerable and expandable ablation devices 16a, 16b extended from the delivery device 15. It should be noted that the delivery device 15 may include a scope, including, but not limited to, an endoscope, laparoscope, catheter, trocar, or other delivery device. For most applications described herein, the delivery device 15 is an endoscope. As shown, the distal tip 28a of the first ablation device 16a is in the delivery configuration (i.e., collapsed shape) and the distal tip 28b of the second ablation device 16b is in the deployed configuration (i.e., expanded shape), illustrating that the ablation devices 16a, 16b can be independently controlled with regard to individual transitioning between delivery and deployed configurations.

As shown, the second ablation device 16b may be coupled to the first ablation device 16a via the pull wire 46. For example, as shown, the pull wire 46 is directly secured at one end to the distal end of the guide sheath 26a of the first ablation device 16a at an anchor point 48. Accordingly, upon application of a force upon the pull wire 46, the distal end of the guide sheath 26a corresponding deflects. The pull wire 46 is further coupled to the second ablation device 16b by way of a loop or hook 50 positioned at a distal end of the guide sheath 26b of the second ablation device 16b through which the pull wire 46 passes. Accordingly, a pulling force upon the pull wire 46 generally results drawing of the distal ends of the guide sheaths 26a, 26b of the first and second ablation devices 16a, 16a towards one another, which will further result in drawing together of the tips 28a, 28b. Accordingly, when both of the tips 28 are in the deployed configurations on opposing sides of a target tissue, a surgeon need only apply a pulling force upon the pull wire 46, which results in drawing of the tips 28a, 28b towards one another, thereby compressing the target tissue between the tips 28a, 28b, at which point, one or both of the tips 28a, 28b can be used to further emit RF energy from their respective electrode arrays, in combination weeping conductive fluid, to create a virtual electrode for subsequent ablation of the target tissue.

Figure 5A:
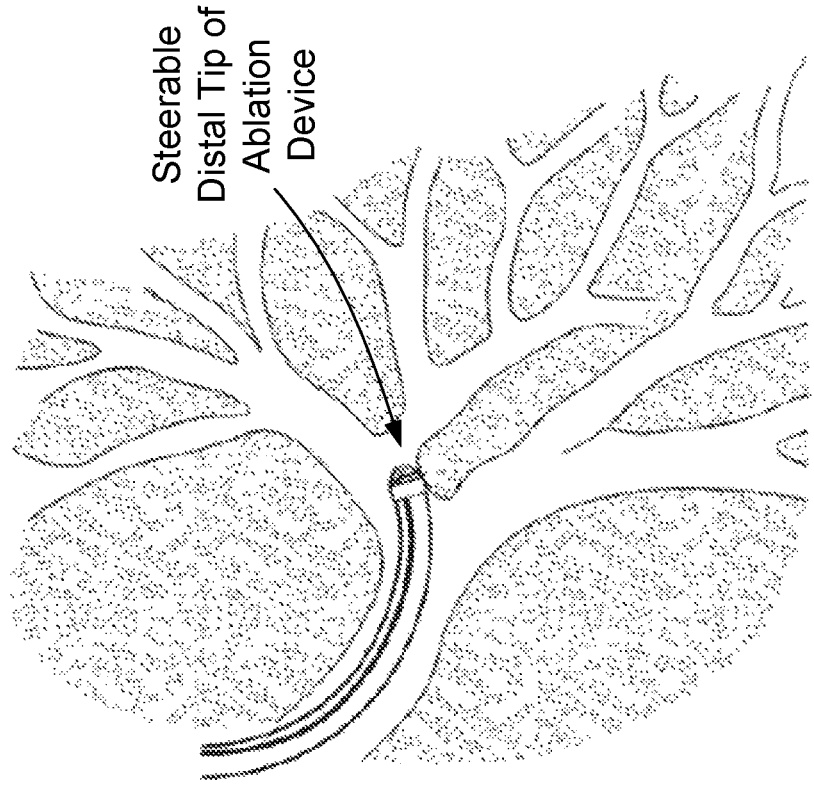
FIGS. 5A and 5B illustrate positioning and movement of the articulating assembly through tortuous pathways within the bronchial airways of a lung, specifically illustrating the steerable nature of at least one ablation device positioned with the delivery device.
Figure 5B:
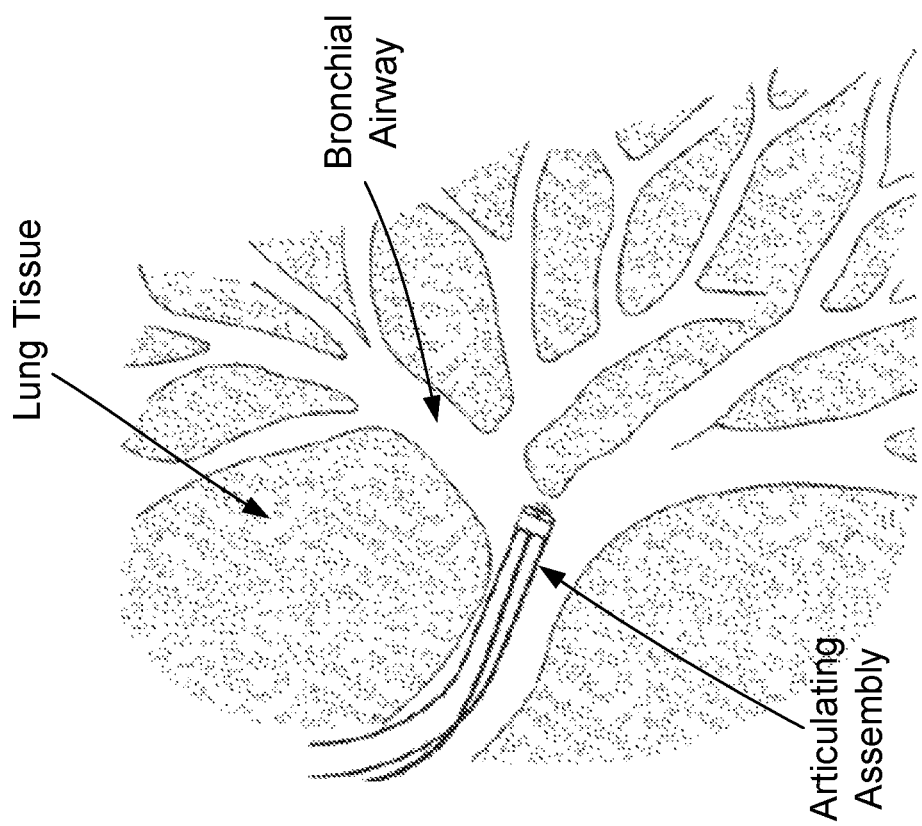

FIGS. 5A and 5B illustrate the positioning and movement of the articulating assembly 14 through tortuous pathways within the bronchial airways of a lung. As previously described, the delivery device may be in the form of a scope and is configured to carry at least two ablation devices 16a, 16b for ablation of a target tissue at a target site within the lung. A surgeon is able to steer the delivery device 15 while advancing the assembly 15 through the bronchial passages of the lung towards the target site which includes diseased tissue, which may include, but is not limited to, a cancerous tumor or emphysema-related damaged tissue. Use of the imaging modality 24 allows for the surgeon to view the assembly 14 during advancement through tortuous anatomy, wherein, upon encountering obstructions, the surgeon can maneuver the scope to continue advancement.

Figure 5C:
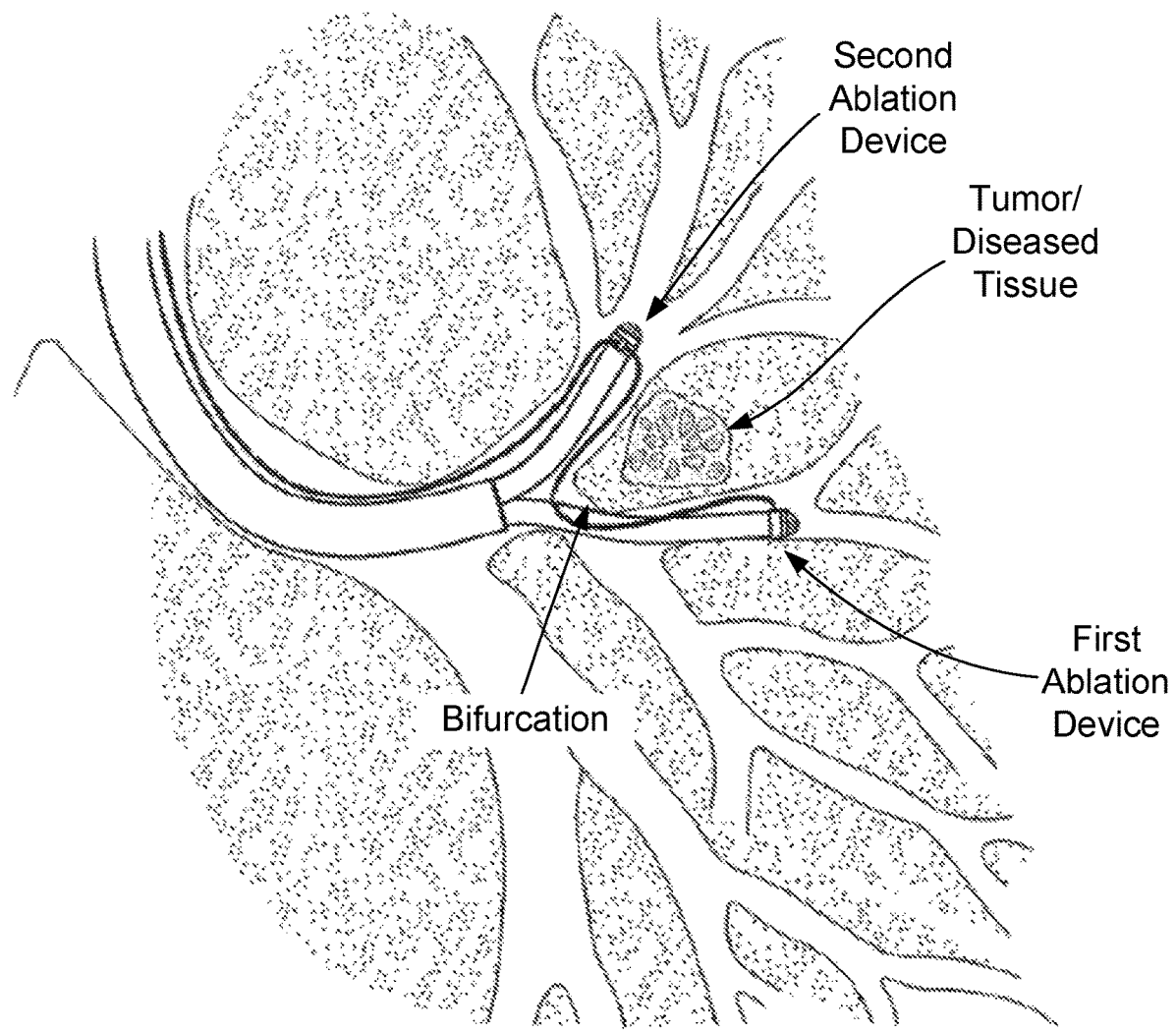
FIG. 5C illustrates positioning of the distal applicator tips of the first and second ablation devices, specifically illustrating independent movement of each applicator tip into a respective pathway extending from a bronchial airway bifurcation and further positioned on sides of a target tissue to be ablated.

Referring to FIG. 5C, upon reaching the target site, which may be located at a bifurcated section of the lung (i.e., at a bronchial airway bifurcation), the surgeon can then begin delivery of the ablation devices 16a, 16b for ablation of the target tissue. For example, as shown, the first ablation device 16a is steerable towards a first pathway extending from the bifurcation and the second ablation device 16b is separately steerable towards a second pathway extending from the bifurcation, such the first and second ablation devices 16a, 16b can be positioned on either side of the target tissue proximate the bifurcation.

Figure 5E:
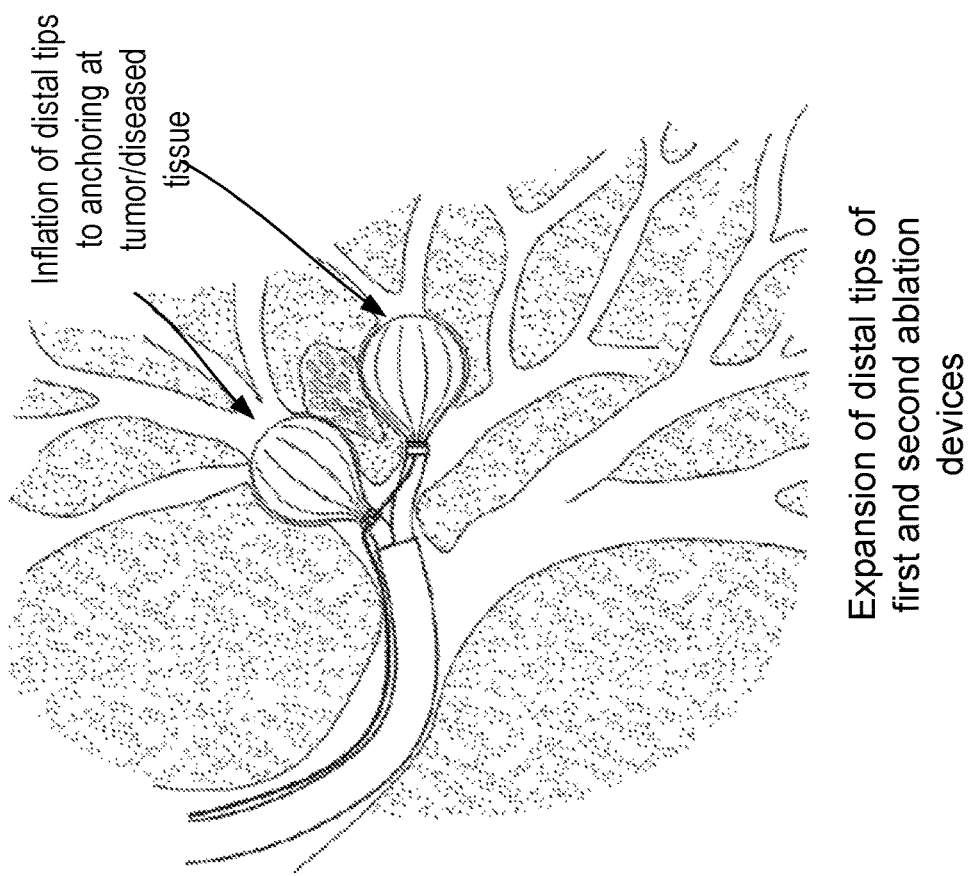
FIG. 5E illustrates transitioning of the distal applicator tips from the delivery configuration to the expanded configuration, expanding in diameter and becoming lodged or anchored within the respective pathways of the bronchial airway and further compressing the target tissue between one another.
Figure 5D:
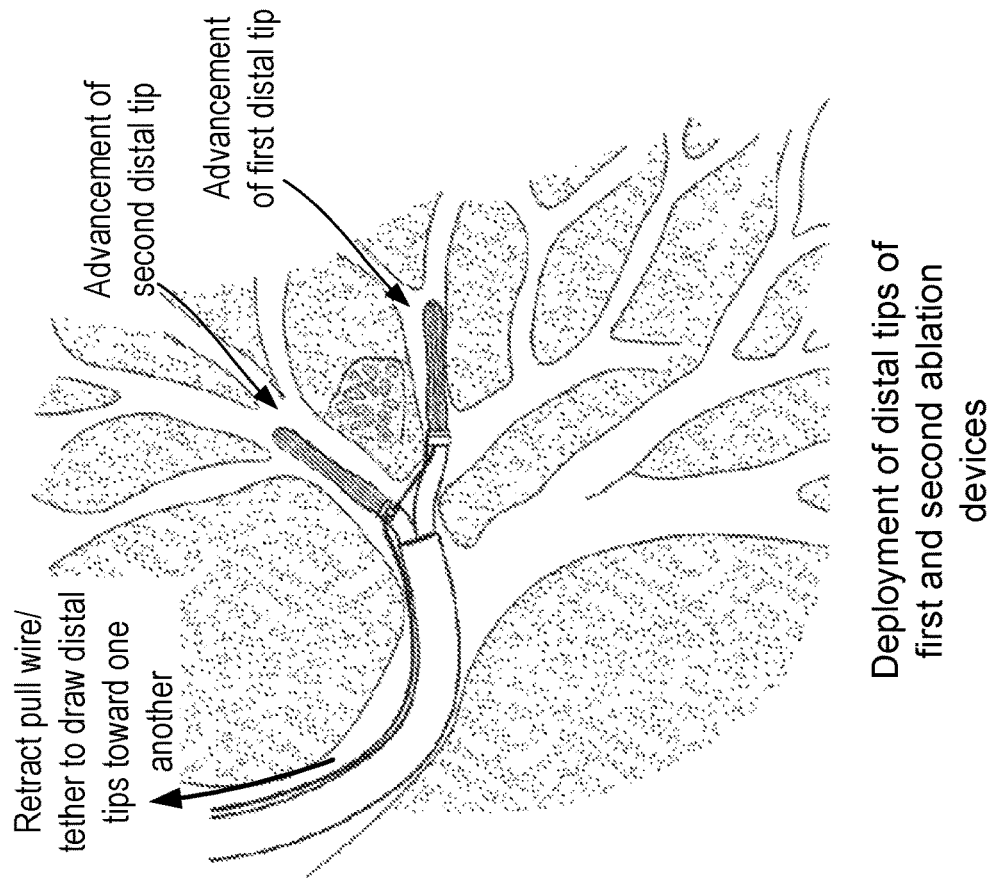
FIG. 5D illustrates deployment of the distal applicator tips of the first and second ablation devices, including advancement of the tips from the respective guide sheaths of the corresponding ablation device, and further illustrates the drawing of the distal applicator tips towards one another based on retraction of a pull wire or tether coupled to both of the ablation devices.
Figure 5G:
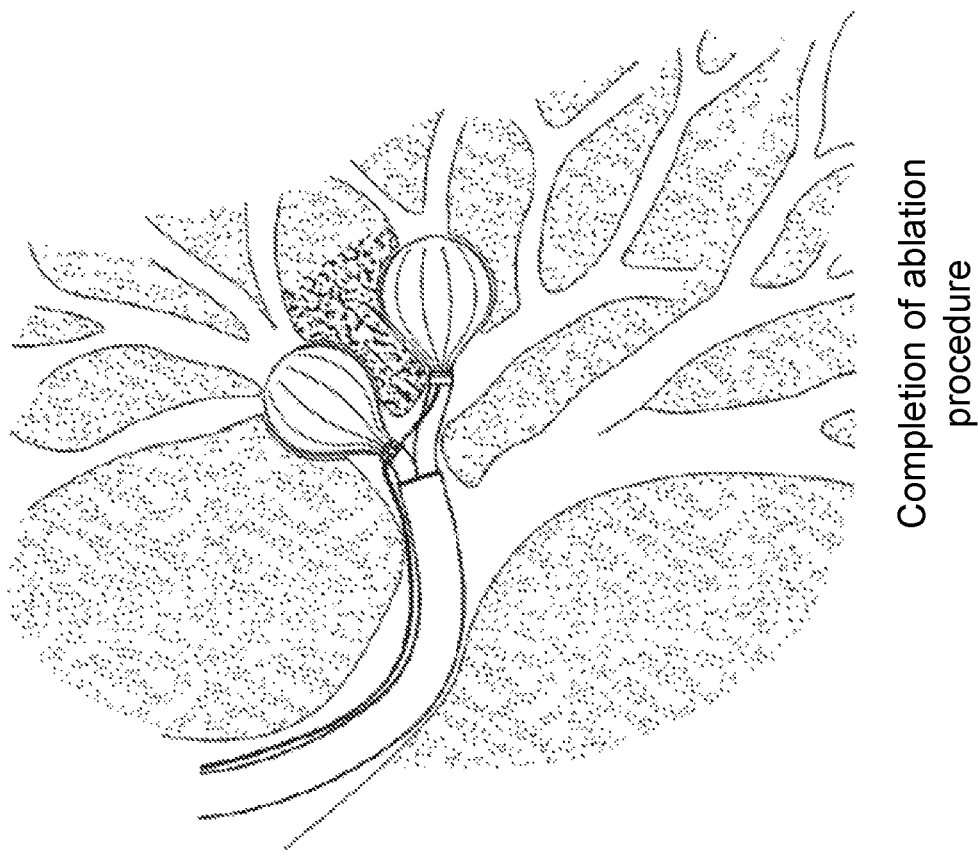
FIG. 5F illustrates the ablation of the target tissue based on the emission of radiofrequency (RF) energy from the distal applicator tips and FIG. 5G illustrates the ablated target tissue.
Figure 5F:
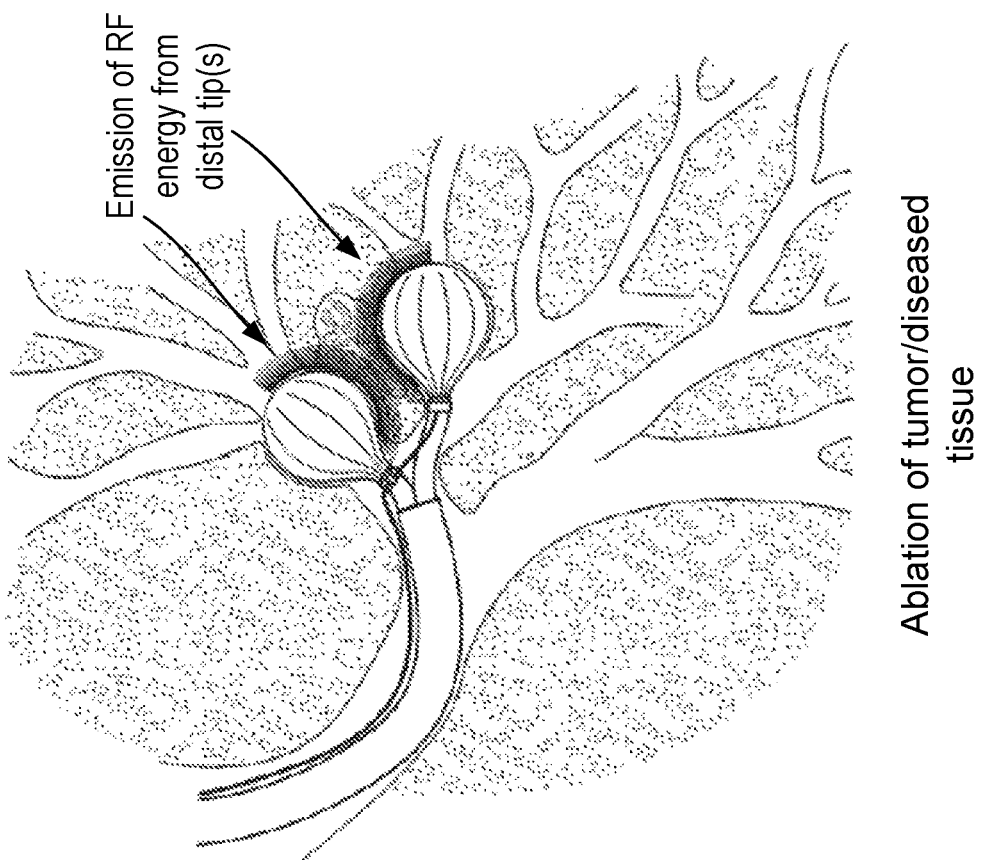

FIG. 5D illustrates deployment of the distal applicator tips 28a, 28b of the first and second ablation devices 16a, 16b, respectively. As shown, a surgeon need only extend each of the tips 28a, 28b from their respective guide sheaths 26a, 26b of the corresponding ablation devices. The surgeon may then retract the pull wire 46, which, as previously described, results in drawing of the tips 28a, 28b towards one another. FIG. 5E illustrates transitioning of the distal applicator tips 28a, 28b from the delivery configuration to the expanded configuration, wherein each tip generally expands in diameter and becomes lodged or anchored within the respective pathways of the bronchial airway. Accordingly, upon expanding, the first and second tips 28a, 28b compress the target tissue between one another. Once positioned and placed in the deployed configurations, ablation may begin. As shown in FIG. 5F, ablation of the target tissue occurs based on the emission of radiofrequency (RF) energy from the distal applicator tips 28a, 28b and FIG. 5G illustrates the ablated target tissue. It should be noted that, in some embodiments, it may be desirable to activate RF emission from only one of the tips, resulting in a directed ablation pattern (i.e., ablation on one side of the target tissue) while the other tip remains in an inactive state and is relied upon as a backstop for maintaining the other active tip in position during ablation.

Figure 6A:
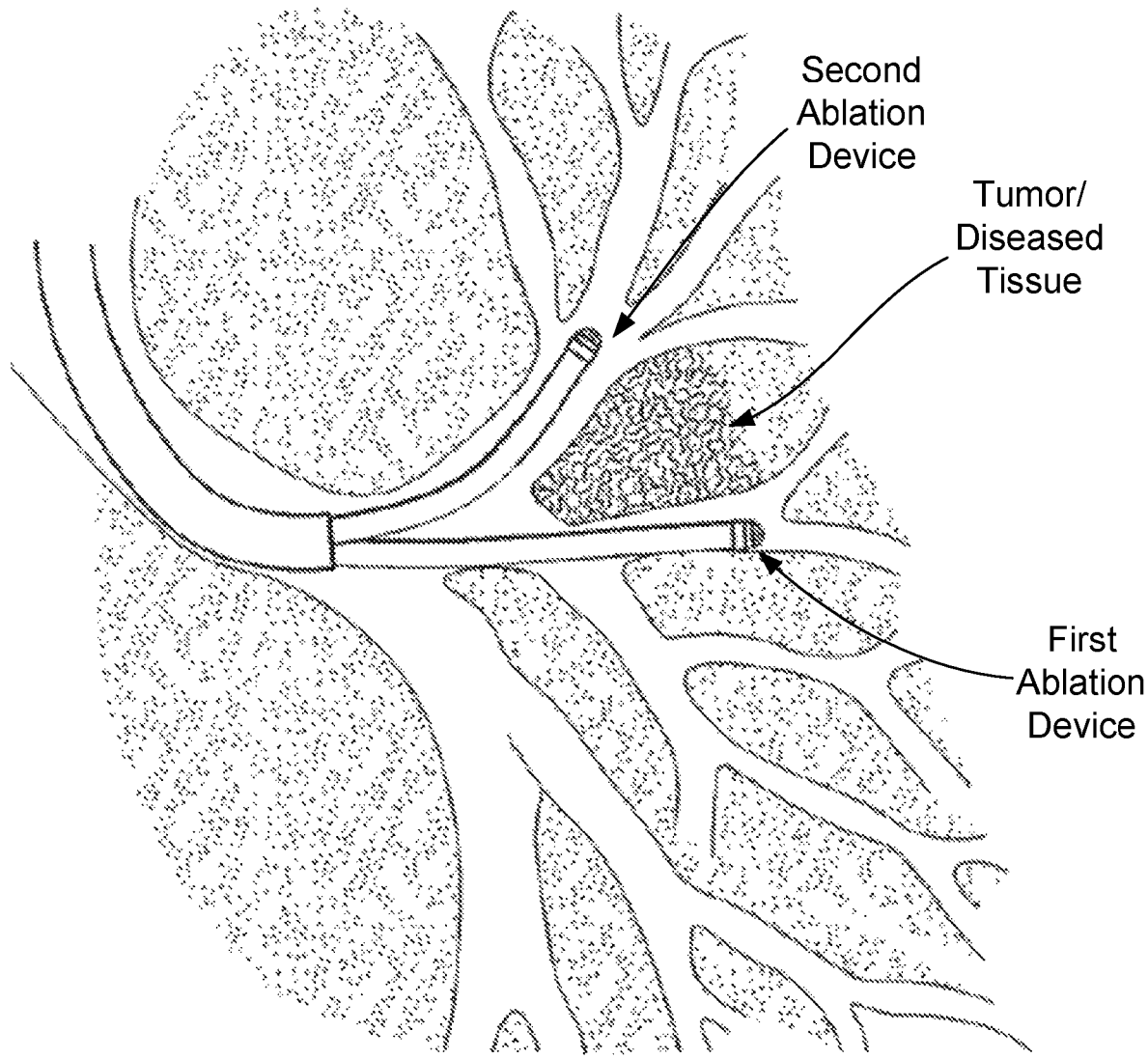
FIGS. 6A, 6B, 6C, and 6D illustrate an articulating assembly having a tetherless designed (i.e., no pull wire or tether coupled to either of the first and second ablation devices)

FIG. 6A-6D illustrate an articulating assembly having a tetherless designed (i.e., the assembly does not include a pull wire or tether coupled to either of the first and second ablation devices). FIG. 6A illustrates positioning of the distal applicator tips of the first and second ablation devices, specifically illustrating independent movement of each applicator tip into a respective pathway extending from a bronchial airway bifurcation and further positioned on sides of a target tissue to be ablated.

Figure 6C:
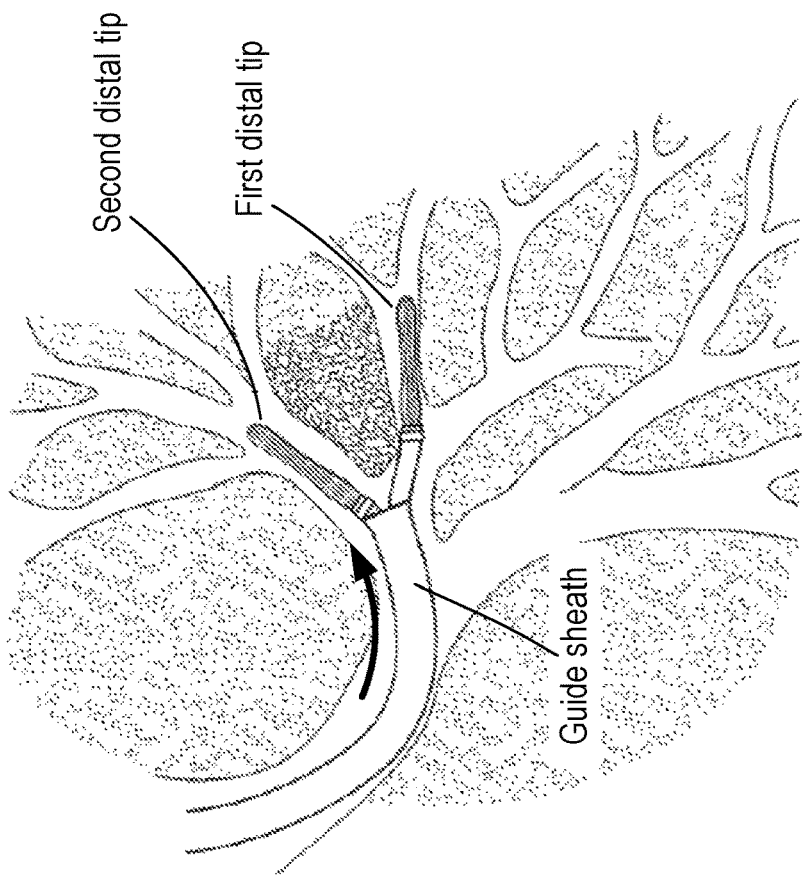
Figure 6B:
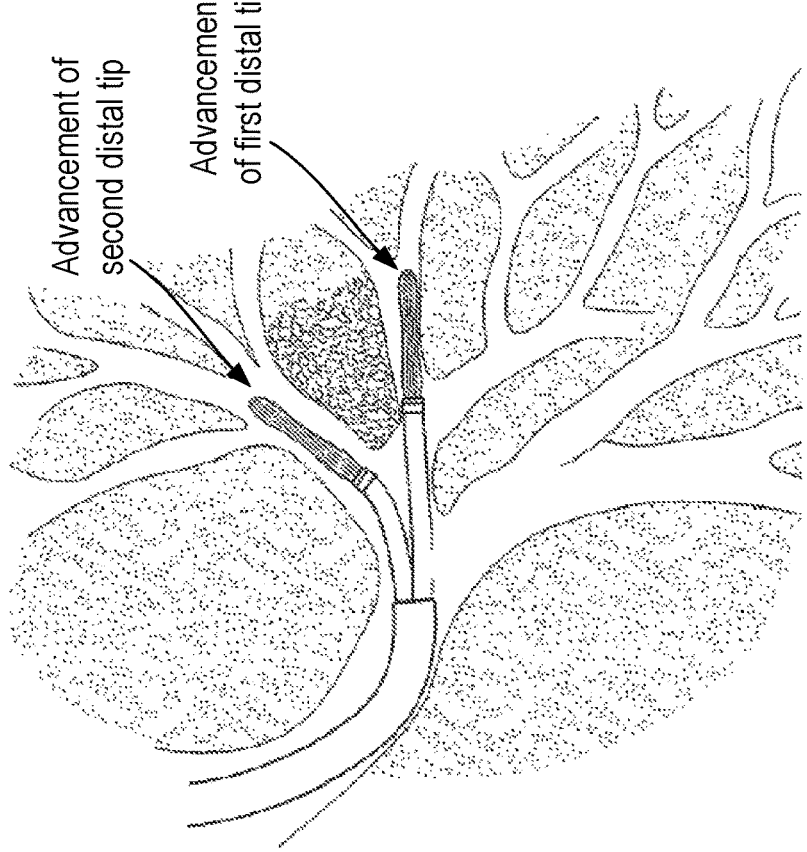
Figure 6D:
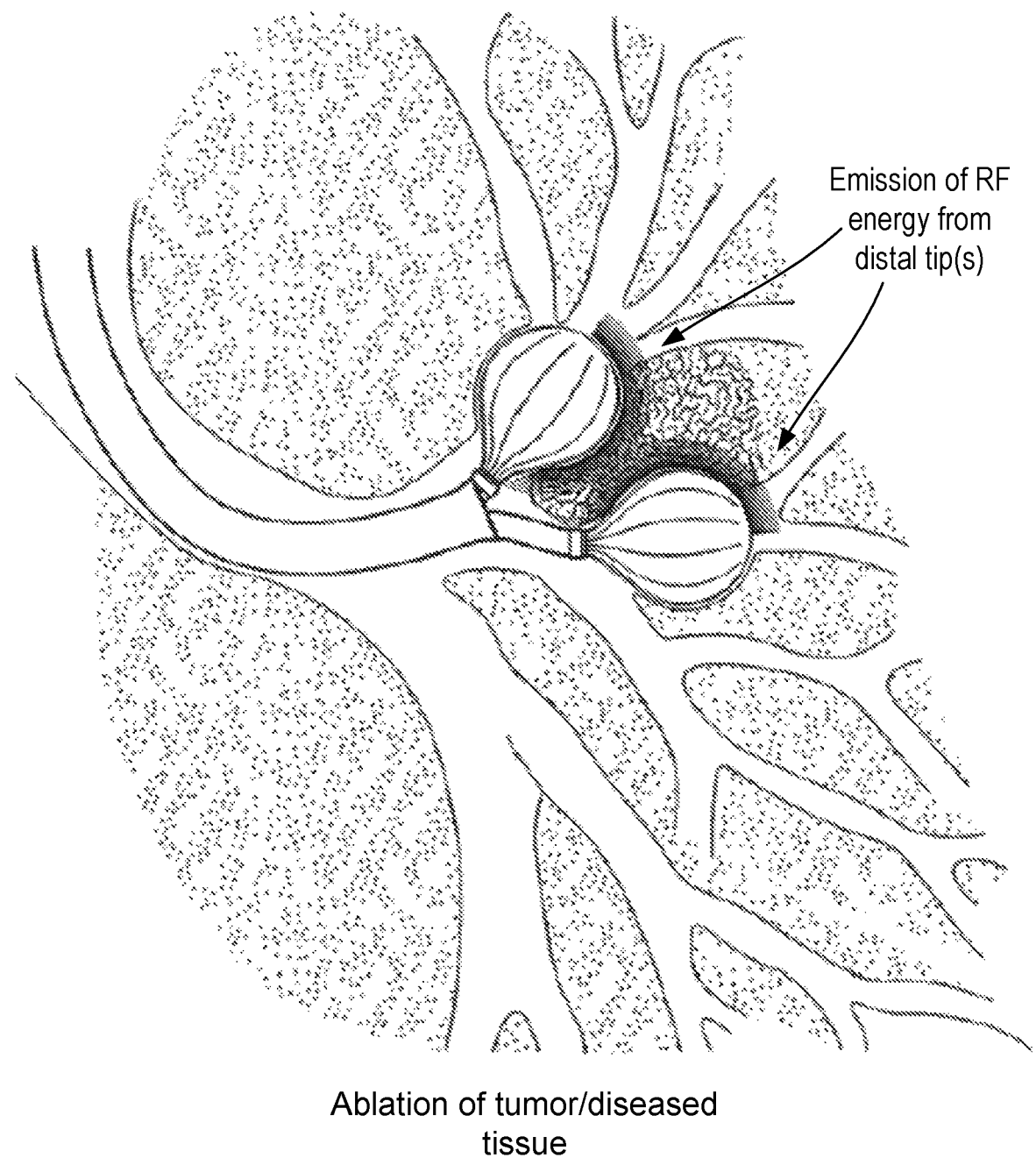

FIG. 6B illustrates deployment of the distal applicator tips of the first and second ablation devices, including advancement of the tips from the respective guide sheaths of the corresponding ablation device. FIG. 6C illustrates the advancement of the outer guide sheath of the delivery device towards the applicator tips, thereby resulting in the drawing of the distal applicator tips towards one another; and FIG. 6D illustrates transitioning of the distal applicator tips from the delivery configuration to the expanded configuration, expanding in diameter and becoming lodged or anchored within the respective pathways of the bronchial airway and further compressing the target tissue between one another and subsequent ablation of the target tissue based on the emission of radiofrequency (RF) energy from the distal applicator tips.

Accordingly, the assembly of the present invention allows for improved controlled over the ablation of tissue, particularly in normally isolated regions ((i.e., tortuous pathways in the lung), allowing for application of RF energy in a controlled manner with little or no deleterious effect on surrounding healthy tissue or organs. Furthermore, the present invention allows for debulking of diseased tissue almost immediately by way of RF ablation, such that, upon treating the diseased tissue, necrosis of such tissue is immediate and the assembly can be completely removed once the procedure is completed, and thus does not present any issues that may be present with devices requiring implantation for a given period of time.

Figure 7:
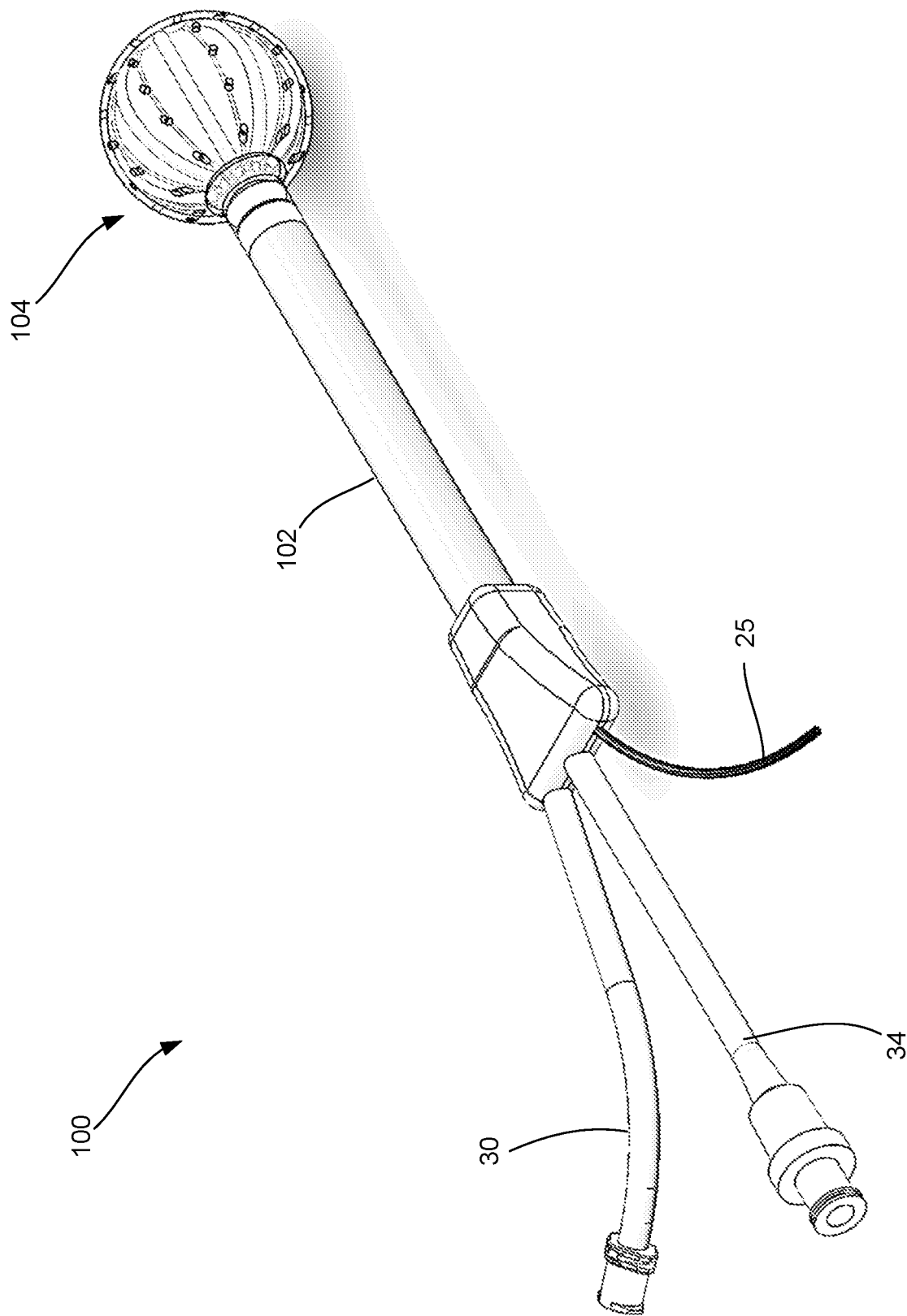
FIG. 7 is a perspective view of one embodiment of a distal applicator tip consistent with the present disclosure.
Figure 8:
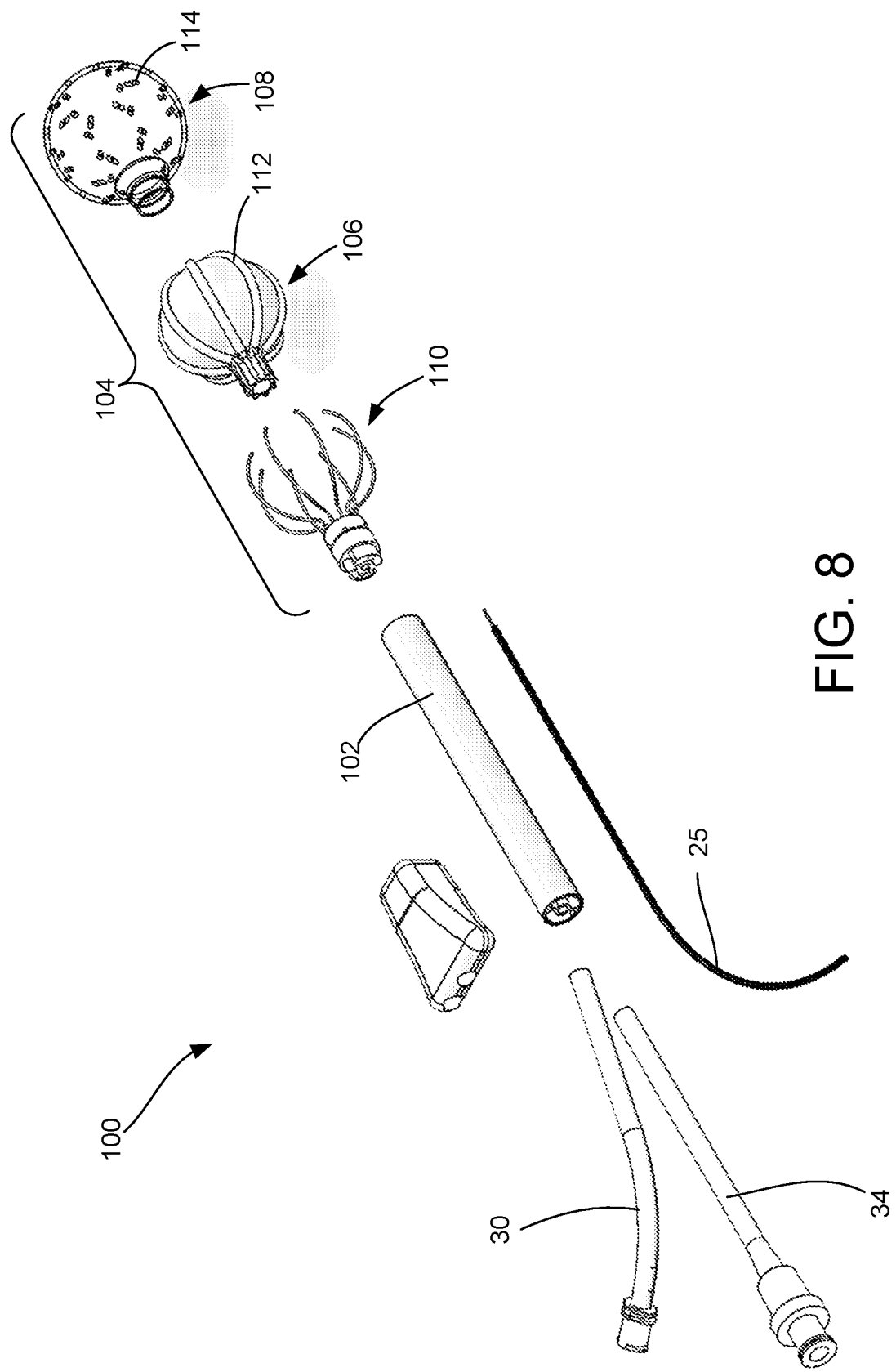
FIG. 8 is an exploded view of the distal application tip of FIG. 7.

FIG. 7 is a perspective view of one embodiment of an ablation device 100 consistent with the present disclosure, including an expandable distal applicator tip 104 extending from a distal end of a handle 102, consistent with the present disclosure. FIG. 8 is an exploded view of the ablation device 100, specifically the distal application tip 104 of FIG. 7. As shown, the applicator tip 104 includes a multiple-balloon design. For example, the applicator tip 104 includes an inner balloon 106 coupled to a first fluid source via a first fluid line 30 and configured to inflate into an expanded configuration in response to the delivery of fluid (e.g., saline, air, etc.) thereto. The applicator tip 104 further includes an outer balloon 108 surrounding the inner balloon 106 and configured to correspondingly expand or collapse in response to expansion or collapse of the inner balloon 106.

The inner balloon 106 may include an irregular outer surface 112, which may include a plurality of bumps, ridges, or other features, configured to maintain separation between the outer surface of the inner balloon 106 and an interior surface of the outer balloon 108, thereby ensuring that a chamber is maintained between the inner and outer balloons. The outer balloon 108 may be coupled to a second fluid source (or the first fluid source) via a second fluid line 34. The outer balloon 108 may further include a plurality of perforations, holes, or ports 114 so as to allow fluid from the second fluid source to pass therethrough, or weep, from the outer balloon 108. The perforations may be sized, shaped, and/or arranged in such a pattern so as to allow a volume of fluid to pass from the chamber to an exterior surface of the outer balloon at a controlled rate.

The applicator tip 104 further includes one or more conductive elements, generally resembling electrically conductive wires or tines 110, positioned within the chamber area between the inner balloon 106 and outer balloon 108. The conductive elements 110 are coupled to the RF generator 20 via an electrical line 25, and configured to conduct electrical current to be carried by the fluid within the chamber from the interior surface to the exterior surface of the outer balloon 108 for ablation of a target tissue, as will be described in greater detail herein. It should be noted that in one embodiment, the plurality of conductive wires 110 may be electrically isolated and independent from one another. This design allows for each conductive wire to receive energy in the form of electrical current from a source (e.g., RF generator) and emit RF energy in response. The system may include a device controller 18, for example, configured to selectively control the supply of electrical current to each of the conductive wires 110.

Figure 9:
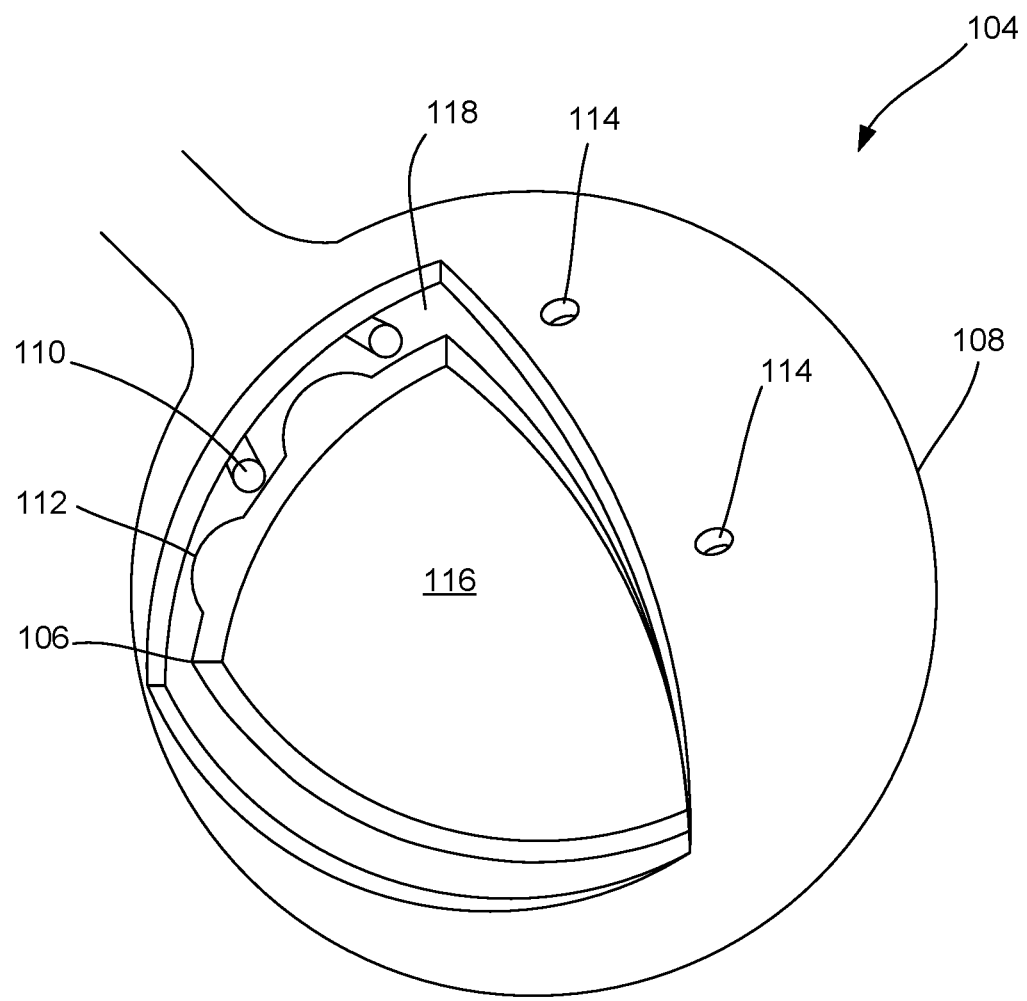
FIG. 9 is a perspective view, partly in section, of the distal applicator tip of FIG. 7.
Figure 10A:
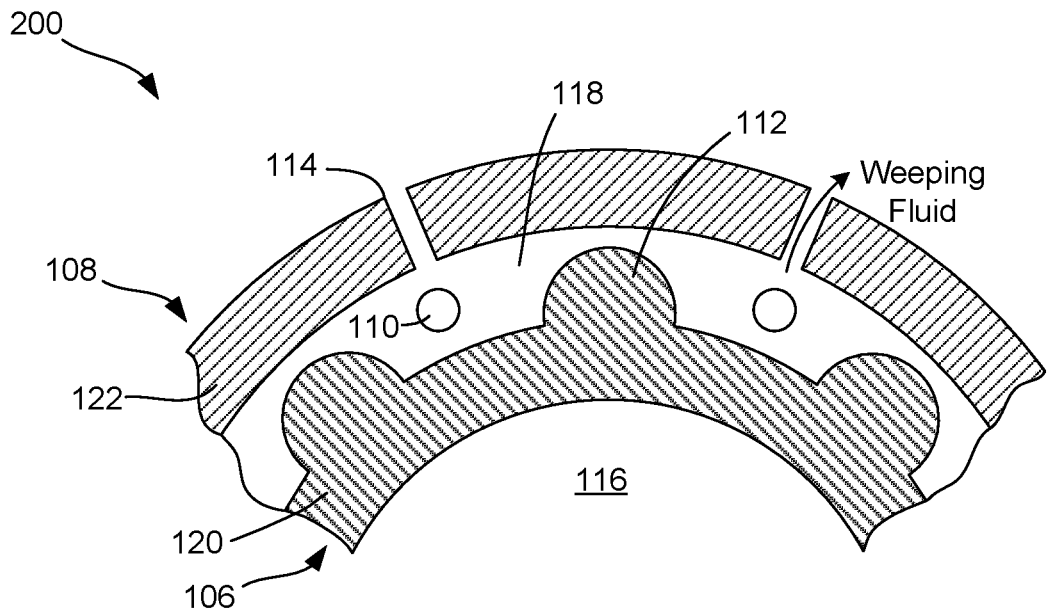
FIGS. 10A and 10B are sectional views of a portion of the distal applicator tip of FIG. 9 illustrating the arrangement of components relative to one another.
Figure 10B:
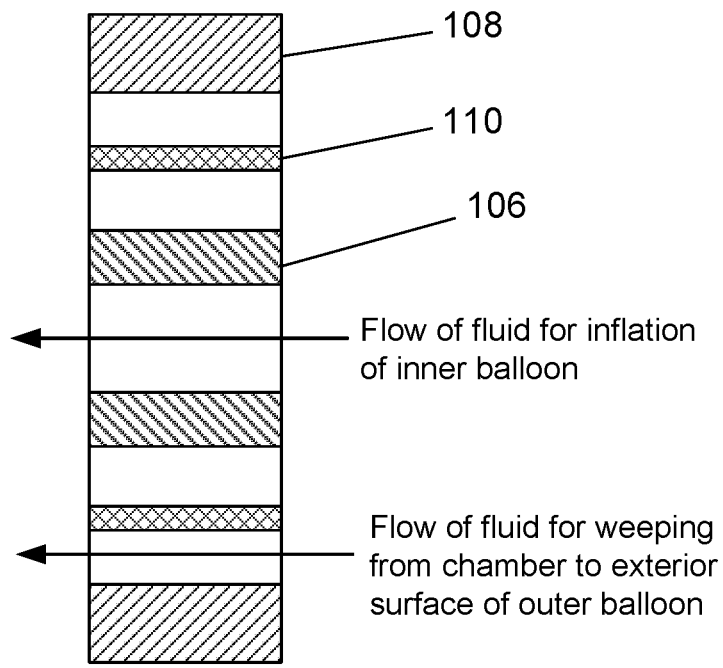

FIG. 9 is a perspective view, partly in section, of the distal applicator tip 104. FIGS. 10A and 10B are sectional views of a portion of the distal applicator tip 104 illustrating the arrangement of components relative to one another.

As shown in FIG. 9, the inner and outer balloons include a chamber 118 defined there between. In particular, the plurality of bumps or ridges 112 arranged on an outer surface of the inner balloon 106 are configured to maintain separation between the outer surface of the inner balloon 202 and an interior surface of the outer balloon 108, thereby ensuring the chamber 118 is maintained.

Once positioned within the target site, a first fluid may be delivered to a lumen 116 of the inner balloon 106, so as to inflate the inner balloon 106 into an expanded configuration, at which point, the outer balloon 108 further expands. A second fluid may then be delivered to the outer balloon 108 such that the second fluid flows within the chamber 118 between the inner and outer balloons 106, 108 and weeps from the outer balloon 108 via the ports 114. Upon activating delivery of RF energy from the conductive elements 110, the RF energy is transmitted from the conductive elements 110 to the outer surface of the outer balloon 108 by way of the fluid weeping from the perforations 114, thereby creating a virtual electrode. For example, the fluid within the chamber 118 and weeping through the perforations 114 on the outer balloon 108 is a conductive fluid (e.g., saline) and thus able to carry electrical current from the active conductive elements 110. Accordingly, upon the fluid weeping through the perforations 114, a pool or thin film of fluid is formed on the exterior surface of the outer balloon 108 and is configured to ablate surrounding tissue via the electrical current carried from the active conductive elements 110. Accordingly, ablation via RF energy is able to occur on the exterior surface of the outer balloon 108 in a controlled manner and does not require direct contact between tissue and the conductive elements 110.

This embodiment is particularly advantageous in that the dual-balloon design does not require a syringe pump, and can be supplied with gravity-fed fluid source 22. In addition, the volume of fluid required within the chamber is significantly less (when compared to a single balloon design), thus less wattage is required to achieve RF ablation. Another advantage of the dual-balloon design of distal tip 104 is that it is not limited to placement within tissue cavities. Rather, when in a collapsed state, the distal tip 104 is shaped and/or sized to fit through working channels of scopes or other access devices, for example, and thus be used for ablation in a plurality of locations within the human body.

It should be further noted that a device 100 of the present disclosure, including the distal tip 104, may further be equipped with feedback capabilities. For example, while in a deflated, collapsed configuration, and prior to saline flow, the tip 104 may be used for the collection of initial data (e.g., temperature and conductivity measurements (impedance measurements) from one or more of the conductive elements 110. Then, upon carrying out the ablation procedure, after certain time ablating, saline flow may be stopped (controlled via controller 18), and subsequent impedance measurements may be taken. The collection of data prior and during an ablation procedure may be processed by the controller 18 so as to provide an estimation of the state of the tissue during an RF ablation procedure, thereby providing an operator (e.g., surgeon) with an accurate indication success of the procedure.

Figure 11:
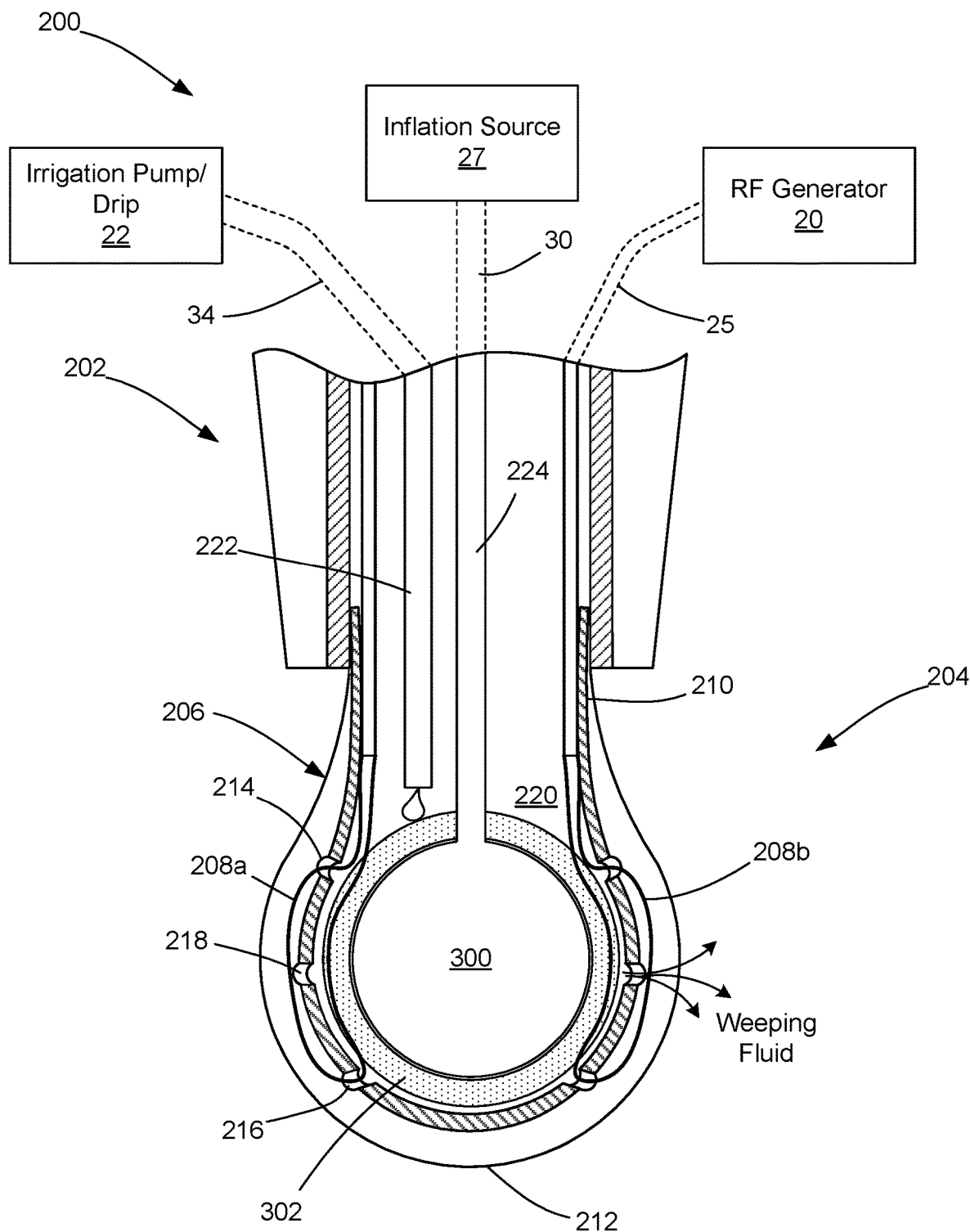
FIG. 11 is side view, partly in section, of another embodiment of a distal applicator tip consistent with the present disclosure.

FIG. 11 is side view, partly in section, of another embodiment of an ablation device 200 consistent with the present disclosure, including an expandable distal applicator tip assembly 204 extending from a distal end of a handle 202, consistent with the present disclosure. The distal applicator tip assembly 204 includes a nonconductive tip 206 extending from a distal end of the handle 202 and an electrode array comprising a plurality of independent conductive wires 208 extending along an external surface of the nonconductive tip 206. As will be described in greater detail herein, the tip assembly 204 is flexible and generally formed from a low durometer material. More specifically, the nonconductive tip 206 and electrode array are generally flexible and configured to transition from a collapsed configuration, in which the tip 206 has a smaller diameter and can be more easily delivered to a target site, to an expanded configuration (e.g., generally spherical) upon a inflation of an inner balloon member. The expansion of the tip assembly 204 allows for the tip assembly to conform to the contour of a target tissue, allowing for improved contact and ablation/coagulation performance.

As shown, the nonconductive tip 206 includes a proximal end 210 coupled to the distal end of the handle 202 and a distal end 212. The nonconductive tip 206 includes a flexible body configured to transition from a collapsed configuration to an expanded configuration upon inflation of an inner balloon member. Upon deflation of the inner balloon member, the nonconductive tip 206 is configured to transition back to the collapsed configuration. Accordingly, the nonconductive tip 206 may include an elastomeric or shape memory material. As shown in FIGS. 3 and 4, the nonconductive tip 206 has a generally spherical shape when in the expanded configuration. Upon application of a force (e.g., pressing of the tip 206 against a target site), the nonconductive tip 206 is configured to flex and transition into a deformed state, where portions of the nonconductive tip 206 can become deformed such that nonconductive tip assumes a compressed shape.

The nonconductive tip 206 includes plurality of proximal ports 214 and distal ports 216 in communication with at least a lumen of the handle 202. The proximal ports 214 and distal ports 216 generally serve as openings through which conductive wires 208 may pass. For example, each of the plurality of wires 208 passes through an associated one of the proximal ports and through a corresponding one of the distal ports. Accordingly, the number of proximal ports 214 and distal ports 216 may generally be equal to the number of conductive wires 208, such that each conductive wire 208 can extend through a different distal port 216, which allows the conductive wires 208 to remain electrically isolated from one another. In other examples, one or more conductive wires can extend through the same distal port 216. The nonconductive tip 206 may further include one or more medial ports 218 configured to allow passage of fluid from the within the nonconductive tip 206 to an external surface of the nonconductive tip 206, as will be described in greater detail herein.

Upon passing through a distal port 216, each conductive wire 208 can extend along an external surface of the nonconductive tip 206. In some examples, the length of the conductive wire 208 extending along the external surface is at least 20% (e.g., at least, 50%, 60%, 75%, 85%, 90%, or 99%) of the length of the nonconductive tip 206. The conductive wire 208 can then re-enter the nonconductive tip 206 through a corresponding proximal port 214. For example, as shown in FIG. 11, conductive wire 208*a* passes through distal port 216, extends along a length of the external surface of the nonconductive tip 206, and passes through an associated proximal port 214 and into a cavity or interior chamber of the nonconductive tip 206, while conductive wire 208*b* is electrically isolated from conductive wire 208*b* in that it passes through its own associated proximal and distal ports. The wires 208 are configured to receive energy in the form of electrical current from the RF generator 20 and emit RF energy in response. The conductive wires 208 can be formed of any suitable conductive material (e.g., a metal such as stainless steel, nitinol, or aluminum).

As shown, one or more of the conductive wires 208 can be electrically isolated from one or more of the remaining conductive wires, such that the electrical isolation enables various operation modes for the device 200. For example, electrical current may be supplied to one or more conductive wires in a bipolar mode, a unipolar mode, or a combination bipolar and unipolar mode. In the unipolar mode, ablation energy is delivered between one or more conductive wires of the electrode array a return electrode, for example. In bipolar mode, energy is delivered between at least two of the conductive wires, while at least one conductive wire remains neutral. In other words, at least, one conductive wire functions as a grounded conductive wire (e.g., electrode) by not delivering energy over at least one conductive wire.

Since each conductive wire 208 in the electrode array is electrically independent, each conductive wire 208 can be connected in a fashion that allows for impedance measurements using bipolar impedance measurement circuits. For example, the conductive wires can be configured in such a fashion that tetrapolar or guarded tetrapolar electrode configurations can be used. For instance, one pair of conductive wires could function as the current driver and the current return, while another pair of conductive wires could function as a voltage measurement pair. Accordingly, a dispersive ground pad can function as current return and voltage references. Their placement dictate the current paths and thus having multiple references can also benefit by providing additional paths for determining the ablation status of the tissue.

As previously described, the ablation device 200 is configured to provide RF ablation via a virtual electrode arrangement. In particular, energy conducted by one or more of the wires 208 is carried by the fluid weeping from the nonconductive tip 206, thereby creating a virtual electrode. For example, the nonconductive tip 206 includes an interior chamber 220 retaining at least an inner balloon member 300 therein, which may essentially act as a spacing member, and a hydrophilic insert 302 surrounding a inner balloon member 300. As shown, the handle 202 includes a fluid lumen 222 coupled to the irrigation pump or drip 22 via the fluid line 34 and is configured to receive conductive fluid therefrom. The hydrophilic insert 302 is configured receive and evenly distribute the conductive fluid from the fluid lumen 222 within the interior chamber 220 by wicking the saline against gravity. The saline within the chamber 220 may be distributed from the hydrophilic insert 302 to an external surface of the tip 206 through the one or more medial ports 218 and/or the other ports (e.g., to the proximal ports 214 and distal ports 216). The saline weeping through the medial ports 218 and/or proximal and distal ports 214, 216 to an outer surface of the nonconductive tip 206 is able to carry electrical current from the electrode array, such that energy is transmitted from the electrode array to a target tissue by way of the saline, thereby creating a virtual electrode.

The handle 202 further includes an inflation lumen 224 configured to be coupled to the inflation source 27 via the connection line 30. Accordingly, the inflatable balloon member 300 is in fluid communication with the inflation source 27 via the inflation lumen 30, such that, when the inflation source is activated, the inner balloon member 300 inflates. Upon inflation, the inner balloon member 300 is shaped and sized so as to maintain the hydrophilic insert 302 in contact with the interior surface of the distal tip wall, and specifically in contact with the one or more ports, such that the hydrophilic insert provides uniformity of saline distribution to one or more of the ports (i.e., at least one of the proximal, distal, and medial ports). Accordingly, upon positioning the distal tip within a target site, the inner balloon member can be inflated to transition the distal tip to the expanded configuration, and the electrode array can be activated. Fluid can then be delivered to the interior chamber, specifically collecting in the hydrophilic insert, and the fluid weeping through the ports to the outer surface of the distal portion is able to carry energy from electrode array, thereby creating a virtual electrode. Accordingly, upon the fluid weeping through the ports, a pool or thin film of fluid is formed on the exterior surface of the distal tip and is configured to ablate surrounding tissue via the RF energy carried from the electrode array.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

Equivalents

Various modifications and further embodiments are possible beyond what is shown and described herein. The subject matter herein contains information, exemplification, and guidance that can be adapted to create various other embodiments.

What is claimed is:

1. A minimally invasive medical assembly for ablating tissue, the assembly comprising:
   a delivery device configured to provide access to a target site within a hollow body of a patient through the tortuous anatomy within a lung, the delivery device comprising a working channel for delivering a pair of ablation devices to the target site;
   wherein each of the pair of individually deliverable ablation devices comprises:
      a nonconductive, expandable distal applicator tip defining an interior chamber and also defining a plurality of ports, at least one of the plurality of ports configured to allow passage of a conductive fluid from the interior chamber to an exterior surface of the distal applicator tip;
      an inflatable member disposed within the interior chamber of the distal applicator tip, the inflatable member configured to transition from a collapsed configuration to an expanded configuration and cause the distal applicator tip to correspondingly transition from a collapsed configuration to an expanded spherical shape; and
      a plurality of conductive wires, wherein each of the plurality of wires passes through one of the plurality of ports such that each of the plurality of wires extends along at least a portion of an exterior surface of the distal applicator tip and passes through one of the plurality of ports into the interior chamber of the distal applicator tip, and is configured to independently conduct energy to be carried by a conductive fluid passing through one or more of the plurality of ports.

2. The assembly of claim 1, wherein the pair of ablation devices are coupled to one another by way of a pull wire.

3. The assembly of claim 2, wherein, upon application of a pulling force upon the pull wire, at least the applicator tips of the ablation devices are configured to correspondingly move relative to one another.

4. The assembly of claim 1, wherein each of the pair of individually deliverable ablation devices further comprises a handle including a lumen for receiving the conductive fluid, wherein the lumen is in fluid communication with the interior chamber of the distal applicator tip.

5. The assembly of claim 1, wherein, upon receipt of an electric current, each of the plurality of conductive wires is configured to conduct radiofrequency (RF) energy to be carried by the conductive fluid passing through one or more of the plurality of ports for ablation of a tissue.

6. The assembly of claim 1, wherein the plurality of ports comprises one or more medial ports for allowing passage of the conductive fluid.

7. The assembly of claim 1, wherein each of the plurality of conductive wires is substantially aligned with at least one of the plurality of ports.

8. The assembly of claim 1, wherein the plurality of ports comprises a plurality of proximal ports and distal ports, wherein each of the plurality of conductive wires passes through at least one of the proximal ports and through a corresponding one of the distal ports such that a portion of each conductive wire has a length that extends along the exterior surface of the distal applicator tip between the corresponding proximal and distal ports.

9. The assembly of claim 8, wherein each of the plurality of proximal ports corresponds to a separate one of the plurality of distal ports such that a portion of a conductive wire passing through a set of corresponding proximal and distal ports has a length that extends along the exterior surface of the distal portion between the corresponding proximal and distal ports.

10. The assembly of claim 1, wherein each of the pair of individually deliverable ablation devices further comprises a hydrophilic member disposed within the interior chamber between an exterior surface of the inflatable member and an interior surface of the distal applicator tip, the hydrophilic member configured to receive and distribute a conductive fluid to the plurality of ports.

11. A minimally invasive medical assembly for ablating tissue, the assembly comprising:
   a delivery device configured to provide access to a target site within a hollow body of a patient through the tortuous anatomy within a lung, the delivery device comprising a working channel for delivering a pair of individually deliverable ablation devices to the target site;
   wherein each of the pair of individually deliverable ablation devices comprises:
      a handle; and
      an expandable assembly extending from the handle, the expandable assembly comprising:
         an inner expandable member configured to transition from a collapsed configuration to an expanded spherical shape, the inner expandable member comprising an exterior surface including a plurality of ridges defined thereon;
         an outer expandable member configured to correspondingly transition from a collapsed configuration to an expanded spherical shape in response to expansion of the inner expandable member, the outer expandable member comprising a plurality of chambers, each chamber is defined between an interior surface of the outer expandable member and the exterior surface of the inner expandable member and a pair of adjacent ridges, the outer expandable member further defining a plurality of ports, at least one of the plurality of ports configured to allow passage of a conductive fluid from the chambers to an exterior surface of the outer expandable member; and
         a plurality of conductive wires, each of which is disposed within a separate respective one of the chambers and configured to independently conduct energy to be carried by a conductive fluid passing through one or more of the plurality of ports.

12. The assembly of claim 11, wherein each of the plurality of ridges is oriented generally along a longitudinal axis of the inner expandable member and the handle.

13. The assembly of claim 11, wherein, upon receipt of an electric current, each of the plurality of conductive wires is configured to conduct radiofrequency (RF) energy to be carried by the conductive fluid passing through one or more of the plurality of ports for ablation of a tissue.

14. The assembly of claim 13, wherein one or more sets of a combination of conductive wires is configured to independently receive an electrical current from an energy source and independently conduct energy.

15. The assembly of claim 13, wherein each of the plurality of conductive wires is substantially aligned with one of the plurality of ports.

16. The assembly of claim 11, wherein the pair of ablation devices are coupled to one another by way of a pull wire.

17. The assembly of claim 16, wherein, upon application of a pulling force upon the pull wire, at least the applicator tips of the ablation devices are configured to correspondingly move relative to one another.

18. The assembly of claim 11, wherein the inner and outer expandable members comprise a non-conductive material.

\* \* \* \* \*